US007181021B2

(12) United States Patent
Raptopoulos et al.

(10) Patent No.: US 7,181,021 B2
(45) Date of Patent: Feb. 20, 2007

(54) APPARATUS FOR ACOUSTICALLY IMPROVING AN ENVIRONMENT

(76) Inventors: Andreas Raptopoulos, 44 Delaford Street, London SW6 7LS (GB); Volkmar Klein, 111 Upper Brockley Road, London SE4 1TF (GB); Dominic Robson, 43 Northway Road, London SE5 9AN (GB); Eugene Scourboutis, Flat 4, Beaumanor Mansions, London W2 4SS (GB); Jeremy Hugh Welter, 208 E. University Pkwy., Baltimore, MD (US) 21218

( * ) Notice: Subject to any disclaimer, the term of this patent is extended or adjusted under 35 U.S.C. 154(b) by 499 days.

(21) Appl. No.: 10/145,113

(22) Filed: May 15, 2002

(65) Prior Publication Data

US 2003/0026436 A1 Feb. 6, 2003

Related U.S. Application Data

(63) Continuation of application No. PCT/GB01/04234, filed on Sep. 21, 2001.

(30) Foreign Application Priority Data

Sep. 21, 2000 (GB) ................................ 0023207.4

(51) Int. Cl.

| | |
|---|---|
| ***A61F 11/06*** | (2006.01) |
| ***H04R 3/00*** | (2006.01) |
| ***H04R 29/00*** | (2006.01) |
| ***H03G 5/00*** | (2006.01) |
| ***H03G 3/00*** | (2006.01) |
| ***G10L 15/04*** | (2006.01) |

(52) U.S. Cl. .................. 381/71.14; 381/103; 381/104; 381/73.1; 381/98; 381/58; 704/251

(58) Field of Classification Search ............... 381/71.1, 381/73.1, 92, 91, 101, 104–109; 704/251
See application file for complete search history.

(56) References Cited

U.S. PATENT DOCUMENTS

| | | | | |
|---|---|---|---|---|
| 4,052,720 | A | | 10/1977 | McGregor et al. |
| 4,438,526 | A | * | 3/1984 | Thomalla ................... 381/73.1 |
| 4,628,530 | A | * | 12/1986 | Op De Beek et al. ...... 381/103 |
| 4,686,693 | A | | 8/1987 | Ritter |
| 5,024,388 | A | | 6/1991 | Kaneko et al. |
| 5,105,377 | A | | 4/1992 | Ziegler, Jr. |
| 5,315,661 | A | | 5/1994 | Gossman et al. |
| 5,355,418 | A | | 10/1994 | Kelsey et al. |
| 5,506,910 | A | * | 4/1996 | Miller et al. ................ 381/103 |
| 5,781,640 | A | | 7/1998 | Nicolino, Jr. |

(Continued)

FOREIGN PATENT DOCUMENTS

| | | |
|---|---|---|
| JP | 03 276998 | 12/1991 |

(Continued)

*Primary Examiner*—Laura A. Grier
(74) *Attorney, Agent, or Firm*—Hunton & Williams LLP

(57) ABSTRACT

The invention provides an apparatus and related method for acoustically improving an environment. In an embodiment of the present invention, an electronic sound screening system includes a portion for receiving acoustic energy and converting it into electrical signals, a portion for performing an analysis of the electrical signals and for generating data analysis signals, a portion responsive to the data analysis signals for producing signals representing sound, and an output portion for converting the sound signals into sound.

40 Claims, 25 Drawing Sheets

U.S. PATENT DOCUMENTS 5,838,802 A * 11/1998 Swinbanks ................. 381/71.2
5,859,914 A * 1/1999 Ono et al. .................... 381/66
5,970,154 A * 10/1999 Chen et al. ................... 381/66
6,556,682 B1 * 4/2003 Gilloire et al. ............... 381/66
6,594,365 B1 * 7/2003 Eatwell ..................... 381/73.1
6,816,599 B2 * 11/2004 Thiede et al. ............... 381/314

FOREIGN PATENT DOCUMENTS

WO WO 01 37256 6/2000
WO WO 01/45082 12/2000

* cited by examiner

APPARATUS FOR ACOUSTICALLY IMPROVING AN ENVIRONMENT

CROSS-REFERENCE TO RELATED APPLICATION

The present application is a continuation of International Application PCT/GB01/04234, with an international filing date of Sep. 21, 2001, published in English under PCT Article 21(2).

BACKGROUND OF THE INVENTION

1. Field of Invention

The present invention relates to an apparatus for acoustically improving an environment, and particularly to an electronic sound screening system for this purpose.

2. Description of Related Art

In order to understand the present invention, it is necessary first to appreciate something of the human auditory system, and the following description is based on known research conclusions and data available in handbooks on the experimental psychology of hearing, and in particular in "Auditory Scene Analysis, The Perceptual Organization of Sound" by Albert S. Bregman, published by MIT Press, Massachusetts.

The human auditory system is overwhelmingly complex, both in design and in function. It comprises thousands of receptors connected by complex neural networks to the auditory cortex in the brain. Different components of incident sound excite different receptors, which in turn channel information towards the auditory cortex through different neural network routes.

The response of an individual receptor to a sound component is not always the same; it depends on various factors such as the spectral make up of the sound signal and the preceding sounds, as these receptors can be tuned to respond to different frequencies and intensities. Furthermore, the neural network route for the sound information can change and so can the destination. All of the above, combined with the sheer number of receptors and neurones connecting them to the auditory cortex, enable the auditory system to decode simple pressure variations to create a highly complex, three-dimensional view of auditory space.

Masking Principles

Masking is an important and well-researched phenomenon in auditory perception. It is defined as the amount (or the process) by which the threshold of audibility for one sound is raised by the presence of another (masking) sound. The principles of masking are based upon the way the ear performs spectral analysis. A frequency-to-place transformation takes place in the inner ear, along the basilar membrane. Distinct regions in the cochlea, each with a set of neural receptors, are tuned to different frequency bands, which are called critical bands. The spectrum of human audition can be divided into several critical bands, which are not equal.

In simultaneous masking the masker and the target sounds coexist. The target sound specifies the critical band. The auditory system "suspects" there is a sound in that region and tries to detect it. If the masker is sufficiently wide and loud, the target sound cannot be heard. This phenomenon can be explained in simple terms on the basis that the presence of a strong noise or tone masker creates an excitation of sufficient strength on the basilar membrane at the critical band location of the inner ear effectively to block the transmission of the weaker signal.

For an average listener, the critical bandwidth can be approximated by:

$$BW_c(f) = 25 + 75\left[1 + 1.4 \cdot \left(\frac{f}{1000}\right)^2\right]^{069} \text{ (Hz)}$$

where $BW_c$ is the critical bandwidth in Hz and f the frequency in Hz.

Also, Bark is associated with frequency f via the following equations:

$$\text{Bark} = \frac{f}{100},\ f > 500 \text{ Hz}$$

$$\text{Bark} = 9 + 4\log_2\frac{f}{100},\ f > 500 \text{ Hz}$$

A masker sound within a critical band has some predictable effect on the perceived detection of sounds in other critical bands. This effect, also known as the spread of masking, can be approximated by a triangular function, which has slopes of +25 and −10 dB per bark (distance of 1 critical band), as shown in accompanying FIG. 23.

Principles of the Perceptual Organization of Sound

The auditory system performs a complex task; sound pressure waves originating from a multiplicity of sources around the listener fuse into a single pressure variation before they enter the ear; in order to form a realistic picture of the surrounding events the listener's auditory system must break down this signal to its constituent parts so that each sound-producing event is identified. This process is based on cues, pieces of information which help the auditory system assign different parts of the signal to different sources, in a process called grouping or auditory object formation. In a complex sound environment there are a number of different cues, which aid listeners to make sense of what they hear.

These cues can be auditory and/or visual or they can be based on knowledge or previous experience. Auditory cues relate to the spectral and temporal characteristics of the blending signals. Different simultaneous sound sources can be distinguished, for example, if their spectral qualities and intensity characteristics, or if their periodicities are different. Visual cues, depending on visual evidence from the sound sources, can also affect the perception of sound.

Auditory scene analysis is a process in which the auditory system takes the mixture of sound that it derives from a complex natural environment and sorts it into packages of acoustic evidence, each probably arising from a single source of sound. It appears that our auditory system works in two ways, by the use of primitive processes of auditory grouping and by governing the listening process by schemas that incorporate our knowledge of familiar sounds.

The primitive process of grouping seems to employ a strategy of first breaking down the incoming array of energy to perform a large number of separate analyses. These are local to particular moments of time and particular frequency regions in the acoustic spectrum. Each region is described in terms of its intensity, its fluctuation pattern, the direction of frequency transitions in it, an estimate of where the sound is coming from in space and perhaps other features. After these numerous separate analyses have been done, the auditory system has the problem of deciding how to group the results so that each group is derived from the same environmental event or sound source.

The grouping has to be done in two dimensions at the least: across the spectrum (simultaneous integration or organization) and across time (temporal grouping or sequential integration). The former, which can also be referred to as spectral integration or fusion, is concerned with the organization of simultaneous components of the complex spectrum into groups, each arising from a single source. The latter (temporal grouping or sequential organization) follows those components in time and groups them into perceptual streams, each arising from a single source again. Only by putting together the right set of frequency components over time can the identity of the different simultaneous signals be recognized.

The primitive process of grouping works in tandem with schema-based organization, which takes into account past learning and experiences as well as attention, and which is therefore linked to higher order processes. Primitive segregation employs neither past learning nor voluntary attention. The relations it creates tend to be valid clues over wide classes of acoustic events. By contrast, schemas relate to particular classes of sounds. They supplement the general knowledge that is packaged in the innate heuristics by using specific learned knowledge.

Grouping

A number of auditory phenomena have been related to the grouping of sounds into auditory streams, including in particular those related to speech perception, the perception of the order and other temporal properties of sound sequences, the combining of evidence from the two ears, the detection of patterns embedded in other sounds, the perception of simultaneous "layers" of sounds (e.g., in music), the perceived continuity of sounds through interrupting noise, perceived timbre and rhythm, and the perception of tonal sequences.

Spectral integration is pertinent to the grouping of simultaneous components in a sound mixture, so that they are treated as arising from the same source. The auditory system looks for correlations or correspondences among parts of the spectrum, which would be unlikely to have occurred by chance. Certain types of relations between simultaneous components can be used as clues for grouping them together. The effect of this grouping is to allow global analyses of factors such as pitch, timbre, loudness, and even spatial origin to be performed on a set of sensory evidence coming from the same environmental event.

Many of the factors that favor the grouping of a sequence of auditory inputs are features that define the similarity and continuity of successive sounds. These include fundamental frequency, temporal proximity, shape of spectrum, intensity, and apparent spatial origin. These characteristics affect the sequential aspect of scene analysis, in other words the use of the temporal structure of sound.

Generally, it appears that the stream forming process follows principles analogous to the principle of grouping by proximity. High tones tend to group with other high tones if they are adequately close in time. In the case of continuous sounds it appears that there is a unit forming process that is sensitive to the discontinuities in sound, particularly to sudden rises in intensity, and that creates unit boundaries when such discontinuities occur. Units can occur in different time scales and smaller units can be embedded in larger ones.

In complex tones, where there are many frequency components, the situation is more complicated as the auditory system estimates the fundamental frequency of the set of harmonics present in sound in order to determine the pitch. The perceptual grouping is affected by the difference in fundamental frequency pitch) and/or by the difference in the average of partials (brightness) in a sound. They both affect the perceptual grouping and the effects are additive.

A pure tone has a different spectral content than a complex tone; so, even if the pitches of the two sounds are the same, the tones will tend to segregate into different groups from one another. However another type of grouping may take effect: a pure tone may, instead of grouping with the entire complex tone following it, group with one of the frequency components of the latter.

Location in space may be another effective similarity, which influences temporal grouping of tones. Primitive scene analysis tends to group sounds that come from the same point in space and segregate those that come from different places. Frequency separation, rate, and the spatial separation combine to influence segregation. Spatial differences seem to have their strongest effect on segregation when they are combined with other differences between the sounds.

In a complex auditory environment where distracting sounds may come from any direction on the horizontal plane, localization seems to be very important, as disrupting the localization of distracting sound sources can weaken the identity of particular streams.

Timbre is another factor that affects the similarity of tones and hence their grouping into streams. The difficulty is that timbre is not a simple one-dimensional property of sounds. One distinct dimension however is brightness. Bright tones have more of their energy concentrated towards high frequencies than dull tones do, since brightness is measured by the mean frequency obtained when all the frequency components are weighted according to their loudness. Sounds with similar brightness will tend to be assigned to the same stream. Timbre is a quality of sound that can be changed in two ways: first by offering synthetic sound components to the mixture, which will fuse with the existing components; and second by capturing components out of a mixture by offering them better components to group with.

Generally speaking, the pattern of peaks and valleys in the spectra of sounds affects their grouping. However there are two types of spectra similarity, when two tones have their harmonics peaking at exactly the same frequencies and when corresponding harmonics are of proportional intensity (if the fundamental frequency of the second tone is double that of the first, then all the peaks in the spectrum would be at double the frequency). Available evidence has shown that both forms of spectra similarity are used in auditory scene analysis to group successive tones.

Continuous sounds seem to hold better as a single stream than discontinuous sounds do. This occurs because the auditory system tends to assume that any sequence that exhibits acoustic continuity has probably arisen from one environmental event.

Competition between different factors results in different organizations; it appears that frequency proximities are competitive and that the system tries to form streams by grouping the elements that bear the greatest resemblance to one another. Because of the competition, an element can be captured out of a sequential grouping by giving it a better sound to group with.

The competition also occurs between different factors that favor grouping. For example in a four tone sequence ABXY if similarity in fundamental frequencies favors the groupings AB and XY, while similarity in spectral peaks favors the grouping AX and BY, then the actual grouping will depend on the relative sizes of the differences.

There is also collaboration as well as competition. If a number of factors all favor the grouping of sounds in the same way, the grouping will be very strong, and the sounds will always be heard as parts of the same stream. The process of collaboration and competition is easy to conceptualize. It is as if each acoustic dimension could vote for a grouping, with the number of votes cast being determined by the degree of similarity with that dimension and by the importance of that dimension. Then streams would be formed, whose elements were grouped by the most votes. Such a voting system is valuable in evaluating a natural environment, in which it is not guaranteed that sounds resembling one another in only one or two ways will always have arisen from the same acoustic source.

Schemas

Primitive processes of scene analysis are assumed to establish basic groupings amongst the sensory evidence, so that the number and the qualities of the sounds that are ultimately perceived are based on these groupings. These groupings are based on rules which take advantage of fairly constant properties of the acoustic world, such as the fact that most sounds tend to be continuous, to change location slowly and to have components that start and end together. However, auditory organization would not be complete if it ended there. The experiences of the listener are also structured by more refined knowledge of particular classes of signals, such as speech, music, animal sounds, machine noises and other familiar sounds of our environment.

This knowledge is captured in units of mental control called schemas. Each schema incorporates information about a particular regularity in our environment. Regularity can occur at different levels of size and spans of time. So, in our knowledge of language we would have one schema for the sound “a”, another for the word “apple”, one for the grammatical structure of a passive sentence, one for the give and take pattern in a conversation and so on.

It is believed that schemas become active when they detect, in the incoming sense data, the particular data that they deal with. Because many of the patterns that schemas look for extend over time, when part of the evidence is present and the schema is activated, it can prepare the perceptual process for the remainder of the pattern. This process is very important for auditory perception, especially for complex or repeated signals like speech. It can be argued that schemas, in the process of making sense of grouped sounds, occupy significant processing power in the brain. This could be one explanation for the distracting strength of intruding speech, a case where schemas are involuntarily activated to process the incoming signal. Limiting the activation of these schemas either by affecting the primitive groupings, which activate them, or by activating other competing schemas less “computationally expensive” for the brain reduces distractions.

There are cases in which primitive grouping processes seem not to be responsible for the perceptual groupings. In these cases schemas select evidence that has not been subdivided by primitive analysis. There are also examples that show another capacity: the ability to regroup evidence that has already been grouped by primitive processes.

Our voluntary attention employs schemas as well. For example, when we are listening carefully for our name being called out among many others in a list we are employing the schema for our name. Anything that is being listened for is part of a schema, and thus whenever attention is accomplishing a task, schemas are participating.

It will be appreciated from the above that the human auditory system is closely attuned to its environment, and unwanted sound or noise has been recognized as a major problem in industrial, office and domestic environments for many years now. Advances in materials technology have provided some solutions. However, the solutions have all addressed the problem in the same way, namely: the sound environment has been improved either by decreasing or by masking noise levels in a controlled space.

Conventional masking systems generally rely on decreasing the signal to noise ratio of distracting sound signals in the environment, by raising the level of the prevailing background sound. A constant component, both in frequency content and amplitude, is introduced into the environment so that peaks in a signal, such as speech, produce a low signal to noise ratio. There is a limitation on the amplitude level of such a steady contribution, defined by the user acceptance: a level of noise that would mask even the higher intruding speech signals would probably be unbearable for prolonged periods. Furthermore this component needs to be wide enough spectrally to cover most possible distracting sounds.

This, relatively inflexible approach, has been regarded hitherto as a major guideline in the design of spaces and/or systems as far as noise distraction is concerned.

SUMMARY OF THE INVENTION

The present invention seeks to provide a more flexible apparatus for, and method of, acoustically improving an environment.

The present invention in a broad sense provides an electronic sound screening system, comprising: means for receiving acoustic energy and converting it into an electrical signal, means for performing an analysis on said electrical signal and for generating data analysis signals, means responsive to the data analysis signals for producing signals representing sound, and output means for converting the sound signal into sound.

Sounds are interpreted as pleasant or unpleasant, that is wanted or unwanted, by the human brain. For ease of reference unwanted sounds are hereinafter referred to as “noise”.

More especially, the invention advantageously employs electronic processes and/or circuitry based on the principles of the human auditory system described above in order to provide a reactive system capable of inhibiting and/or prohibiting the effective communication of such noise by means of an output which is variably dependent on the noise.

The means for performing the analysis and generating sound signals may include a microprocessor or digital signal processor (DSP). A desktop or laptop computer can also be used. In either case, an algorithm is preferably employed to define the response of the apparatus to sensed noise. Sound generation is then advantageously based on such an algorithm, contained in the processor or computer chip.

The algorithm advantageously works on the basis of performing an analysis of the ambient noise in order to create a more pleasing sound environment. The algorithm analyses the structural elements of the ambient noise and employs the results of the analysis to generate an output representing tonal sequences in order to produce a pleasant sound environment.

Several experimental case studies have been carried out in different situations/locations with diverse sound/noise environments. Digital recordings were made and the sound signals were then played back in different locations. The sound signals were also analyzed with spectrograms and their results were compared to spectrograms of pieces of music and recordings of natural sounds. The analysis of the data then resulted in design criteria that were incorporated into the algorithm. The algorithm preferably tunes the sound signal by analyzing, in real time, incoming noise and produces a sound output which can be tuned by the user to match different environments, activities or aesthetic preferences.

The apparatus may have a partitioning device in the form of a flexible curtain. However, it will be appreciated that such device may also be solid. The curtain may be as described in International Patent Application No. PCT/GB00/02360, which is incorporated herein by reference.

The electronic sound screening system of the present invention provides a pleasant sound environment by analyzing noise to generate non-disturbing sound.

The partitioning device in the preferred embodiment as described below can be seen as a smart textile that has a passive and an active element incorporated therein. The passive element acts as a sound absorber bringing the noise level down by several decibels. The active element generates pleasant sound based on the remaining noise. The latter is achieved by recording and then processing the original noise signal with the use of an electronic system. The generated sound signal may then be played back through speakers connected to the partitioning device.

In a preferred embodiment, the algorithm is modeled on the human auditory perception system.

In particular, following the described architecture of human auditory perception, the present electronic sound system preferably comprises a masker and a tonal engine. The masker is designed to interfere with the physiological process of the human auditory system by rendering certain parts of the spectrum of the sensed noise inaudible. The tonal engine is designed to interfere with the perceptual organization of sound employing auditory stream segregation or separation and potentially interacting with schemas of memory and knowledge. Thus, on one level, the tonal engine aims to add "confusing" information to the ambient sound, which can group with existing cues to form new auditory streams, and on another level it aims to direct attention away from unwanted signals by providing a preferred sound signal for the listener to engage with.

Advantageously, in the case of both the masker and the tonal engine, control inputs are provided so that listeners, by exercising control, can vary certain functional characteristics according to their particular preferences.

In some preferred embodiments, the masker may also utilize schemas, when for example the output of the masker is chosen to have richer musical qualities. Accordingly the tonal component interferes with primitive processes of grouping when for example random gliding melodies mask or alter phonemes.

The principle of operation of the masking component of the electronic sound system preferably relies on the automatic regulation of the spectral content and amplitude level of the output relative to the spectral content of the sensed noise. More particularly, the masker tracks prominent frequencies in the sensed noise and assigns masking signals to them that have an optimized frequency and amplitude relationship with the masked signals, as calculated on the basis of analytical expressions applicable for the simultaneous masking of tone-from-noise and nose-from-tone, when the spread of masking beyond the critical band is also taken into account.

This real-time regulating system enables the masker output effectively to mask prominent frequencies that constitute acoustic distraction, while minimizing its energy requirement.

It is an advantage of the invention at least in its preferred form described below that the masker can reach instantaneous amplitude levels significantly higher than the ones normally afforded by conventional systems at times of peak activity; and conversely at times of little activity, the contribution can drop and still ensure an adequately low signal to noise ratio.

Furthermore, the masker sound in the described embodiments encompasses musical structure, which further increases the level of user acceptance to the masker sounds. The output of the masker is preferably built on a proposed chord root from the tonal engine as a series of notes whose exact frequencies and amplitudes are tuned to mask traced prominent frequencies on the basis of the well documented masking principles.

The masker can be tuned to provide a virtually steady sound environment or one which is very responsive. The latter can be achieved if the masker is set to track a very high number of prominent frequencies and not build its output on the proposed chord root; in this case an output may be achieved which can effectively mask all speech signals.

Several user settings in the preferred embodiment conveniently allow listeners to tune the system for their particular preferences and taste. These may include, for example, minimum and maximum amplitude levels, sensitivity of the output to a sudden increase of the input, hue of the masker sound (wind, sea or organ) and others.

These user settings can then be captured if desired for subsequent re-use at any time.

The tonal engine is preferably arranged to provide an output designed to interfere with higher processes employing auditory stream segregation or separation and to interact with schemas of memory and knowledge.

In the preferred embodiment described below, the tonal engine output comprises a selective mixing of various, for example eight, different 'voices', i.e. tonal sequences, which are used for different purposes.

A number of these, for example two, are advantageously used to introduce pace and rhythm into the sound environment. These tonal sequences are designed to generate auditory cues that are clearly separate from the auditory cues that are prominent to the sound environment. Preferably, these tonal sequences are not responsive to sensed sound, but are responsive directly to user preference via settings of the harmonic characteristics. They may encompass musical meaning, as indicated below.

Another subset, for example two, of the tonal sequences, is advantageously responsive to sensed input and output tones and is designed to interfere with the process of object formation in the auditory cortex. These tonal sequences can be used in two ways:

Firstly, they can be tuned so as to group with prominent acoustic streams, usually streams with rich informational content variant over time, such as speech. In this way, a "new" stream may be created whose informational content is poorer or whose sound identity is more controlled so as to be perceived as less distracting.

Such tonal sequences can interact directly with prominent signals such as speech in order to disrupt intelligibility. By adding frequency components, which can group with complex sounds or with components of these sounds, the tonal sequences may interfere with the process of primitive grouping such that frequency grouping is incomplete. This may result in sounds either that are not recognizable (e.g. when speech is the target stream) or that are less irritating (e.g. in the case of individual distracting sounds).

The sound screening system according to the present invention affects distracting perceptual signals and streams and decreases their clarity by hindering the mechanisms that aid the segregation of such signals. By "weakening" the robustness of such streams, their content will become less recognizable and hence less distracting.

Secondly, these tonal sequences can be designed to output a recognizable and clearly separate acoustic stream, which is designed to become more prominent when acoustic streams of the sensed noise environment become more prominent. This may be achieved by linking the amplitude of the output streams to the amplitude of the sensed noise, for example, in a particular part of the spectrum where auditory activity is noticeable. When the activity in the sensed sound increases, the output auditory streams of the tonal engine are also arranged to become more prominent in order to redirect attention or allow the listener to stay perceptually connected to them.

A further subset, for example four, of the tonal sequences are motive voices that are triggered by prominent sound events in the acoustical environment. Each tonal sequence can be perceived as an auditory cue that attempts by itself to capture attention and that involves schema activation. This tonal output can be tuned not to blend with the distracting sound streams, but rather remain a separate auditory cue that the listener's attention focuses on subconsciously. Such an output would be used to redirect attention.

Each motive voice can be tuned to generate a stream of sound in a different frequency band of the auditory spectrum, being activated by a decision-making process relative to the activity in this particular band. The decision making process may rely on simple temporal and spectral modeling, similar to, but much simpler than the process of the human auditory system. This process conveniently effects a mapping of sound events in the auditory world to the tonal outputs of the tonal engine. It may also involve complex artificial intelligence techniques for making qualitative decisions that can be used to distinguish speech from other sources of noise distraction, the voice of one speaker from the voice of another, telephone rings from door slams etc.

These four motive voices or tonal sequences are a tool of great value for introducing aesthetic control, taste and emotion to the sound environment. Users can choose the sound outputs that respond best to their needs at any time and can introduce control in their acoustic environment by linking prominent, generally unpleasant, sound events in the environment that they have no control over with pleasant sound events that they select.

The study of the mechanisms of human auditory perception has thus provided guidelines for the creation of tonal sequences according to the invention, in order for them not to constitute a sound distraction in themselves.

Furthermore, a comprehensive interface has been created according to the invention for the tuning of different parameters that relate not only to the use of the analysis data for the sensed noise but also in the musical structure of the output.

The motive voices may also provide a rich interface between the audio or non-audio environment that is external to the user and the immediate acoustic environment as perceived by the user. Through the triggering of separate sound events, as they initiate them, users can become aware of changes in the immediate or distant environment and can communicate with this, without necessarily disrupting their work process activity.

Furthermore, the sound screening system according to the invention may be equipped with an RF (that is with a radio frequency) or other wireless connection to receive parameters transmitted by a local station installed on site. Such parameters may be audio or non-audio parameters. The system can then be configured to respond to transmitted information considered to be important to the users or their organizations. Software may be employed to customize the system for this purpose.

The sound screening system according to the invention may also be arranged to receive information from the Internet. A service provider can host a site on the web that would contain several information parameters that could be chosen to influence the behavior of the system (personal or communal, small or large scale). These could be geographical location, nature of work tasks in a work environment, age, character, date (absolute and relative, i.e. weekday, weekend, holiday, summer, winter), weather, even the stock market index. The users may select which of these parameters they want to determine the behavior of their system and they may also define how these parameters are to be mapped to the system's behavior.

Sets of parameters can then be downloaded to the system, sent to the device via RF from local stations or obtained from the Internet, for determining the response of the system.

The sound screening system according to the invention may also be arranged to sense in real time parameters (audio and non-audio) that affect its response and thereby enable the users to become aware of changes in their environment. Examples of sensors and/or data providers that can be used to derive information from the environment to define the response of the system include proximity sensors, pressure sensors, barometers and other sensory devices that can communicate with the system and define its audio behavior.

Such parameters may also be used to enrich other interactive qualities of the sound screening system as well. For example, by using a proximity sensor in the vicinity, the system can be programmed to become gradually silent when somebody is steadily approaching.

The term "preset" is used here to denote a set of parameters that define the behavior of the electronic sound system according to the invention. A preset is thus a carrier of information, which defines the behavior of the system. Presets can be used in very diverse ways. For example, they can even determine a mood transmitted through a certain sound output.

Specially designed software can be downloaded to a system PC in order to allow users to have access to the full functionality and tuneability of the algorithm and to generate presets that can be used later. A site on the web can be set up to sell presets developed by auditory experts, with the specialist knowledge of the system. Connections to the central processing unit or the controller of the electronic sound system, for downloading or exchanging presets, may be established in many ways, for example using wireless (Radio Frequency or Infrared) or wire connections (USB or other) or using peripherals like memory cards, existing or custom-made.

In particular, a memory card, can be used for downloading information to and from the system PC. Such a memory card may be interfaced with the PC by way of a device (a PC peripheral), which is sold as an accessory, housing a receptor for the memory card. The memory card may then be seen as the physical manifestation of the preset.

A memory card may even provide a feedback control link offering a range of options between ultimate control and limited controllability. It may allow users not only to create presets in the system, with control over different levels of the algorithm, but also to define the mapping of those parameters to the response of the system. Ultimately the behavior of the system and control over it may be customized via the memory card.

It is also possible to omit the masker altogether, and therefore another aspect of the invention features an electronic sound screening system comprising: means for receiving a control input representing sound parameters, means for responsive to the control input for providing corresponding control signals, a plurality of sound generators responsive to the control signals for generating tonal sequence signals representing tonal sequences, and output means for converting the tonal sequence signals into sound.

The invention has a myriad of applications. For example, it may be used in shops, offices, hospitals or schools as an active noise treatment system.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the following descriptions taken in connection with the accompanying drawings in which.

DETAILED DESCRIPTION OF THE PREFERRED EMBODIMENTS

Figure 1:
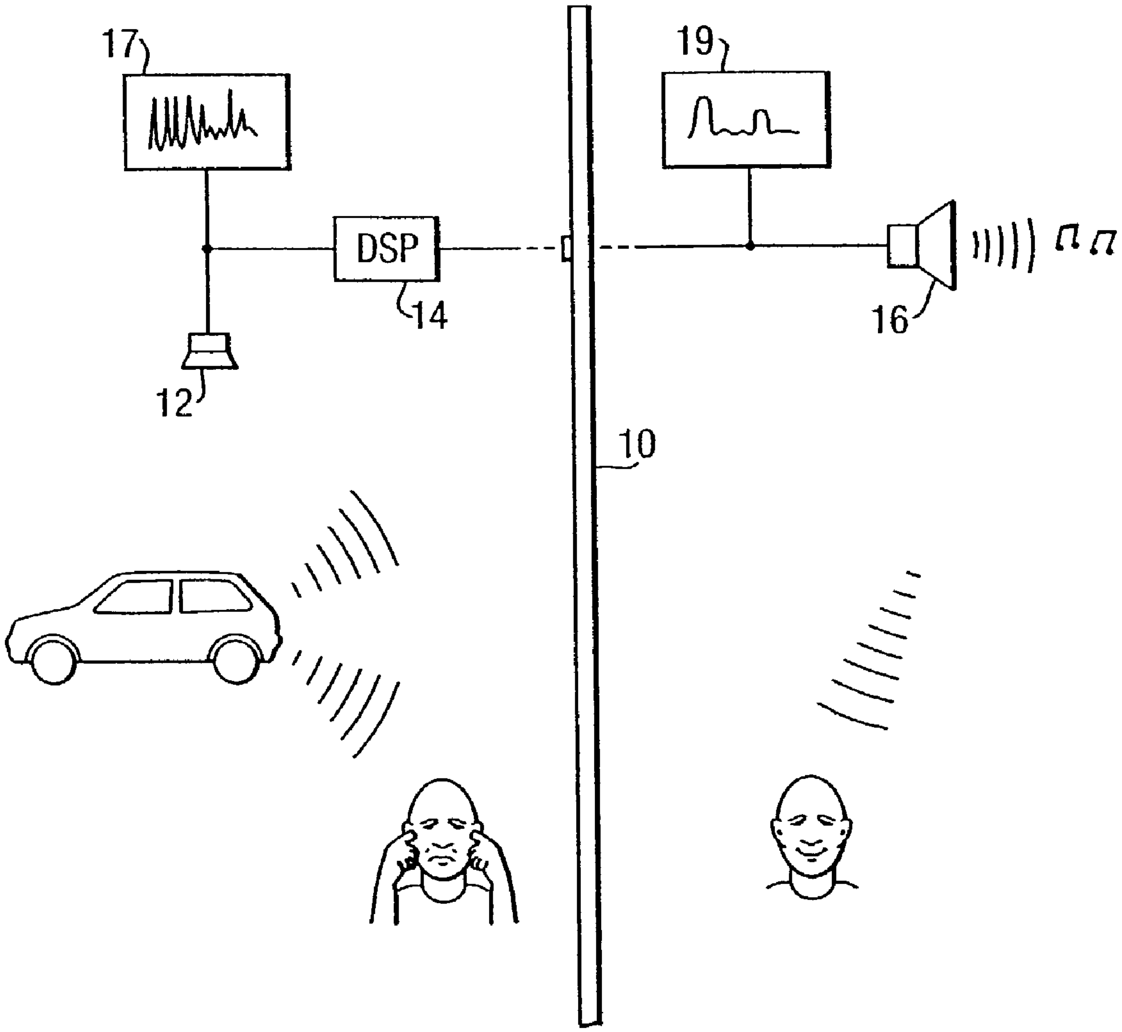
FIG. 1 is a general schematic diagram illustrating the operation of the invention.

Preferred embodiments of the present invention and their advantages may be understood by referring to FIGS. 1–23, wherein like reference numerals refer to like elements. The inventive concept is directed to acoustically improving a sound environment.

Referring initially to FIG. 1, there is shown generally an apparatus for acoustically improving an environment, which apparatus comprises a partitioning device in the form of a curtain 10. The apparatus also comprises a number of microphones 12, which may be positioned at a distance from the curtain 10 or which may be mounted on, or integrally formed in, a surface of the curtain 10. The microphones 12 are electrically connected to a digital signal processor (DSP) 14 and thence to a number of loudspeakers 16, which again may be positioned at a distance from the curtain or mounted on, or integrally formed in, a surface of the curtain 10. The curtain 10 produces a discontinuity in a sound conducting medium, such as air, and acts primarily as a sound absorbing device.

The microphones 12 receive ambient noise from the surrounding environment and convert such noise into electrical signals for supply to the DSP 14. A spectrogram 17 representing such noise is illustrated in FIG. 1. The DSP 14 employs an algorithm firstly for performing an analysis of such electrical signals to generate data analysis signals, and thence in response to such data analysis signals for producing sound signals for supply to the loudspeakers 16. A spectrogram 19 representing such sound signals is illustrated in FIG. 1. The sound issuing from the loudspeakers 16 is preferably an acoustic signal based on the analysis of the original ambient noise, for example from which certain frequencies have been selected to generate sounds having a pleasing quality.

Figure 2:
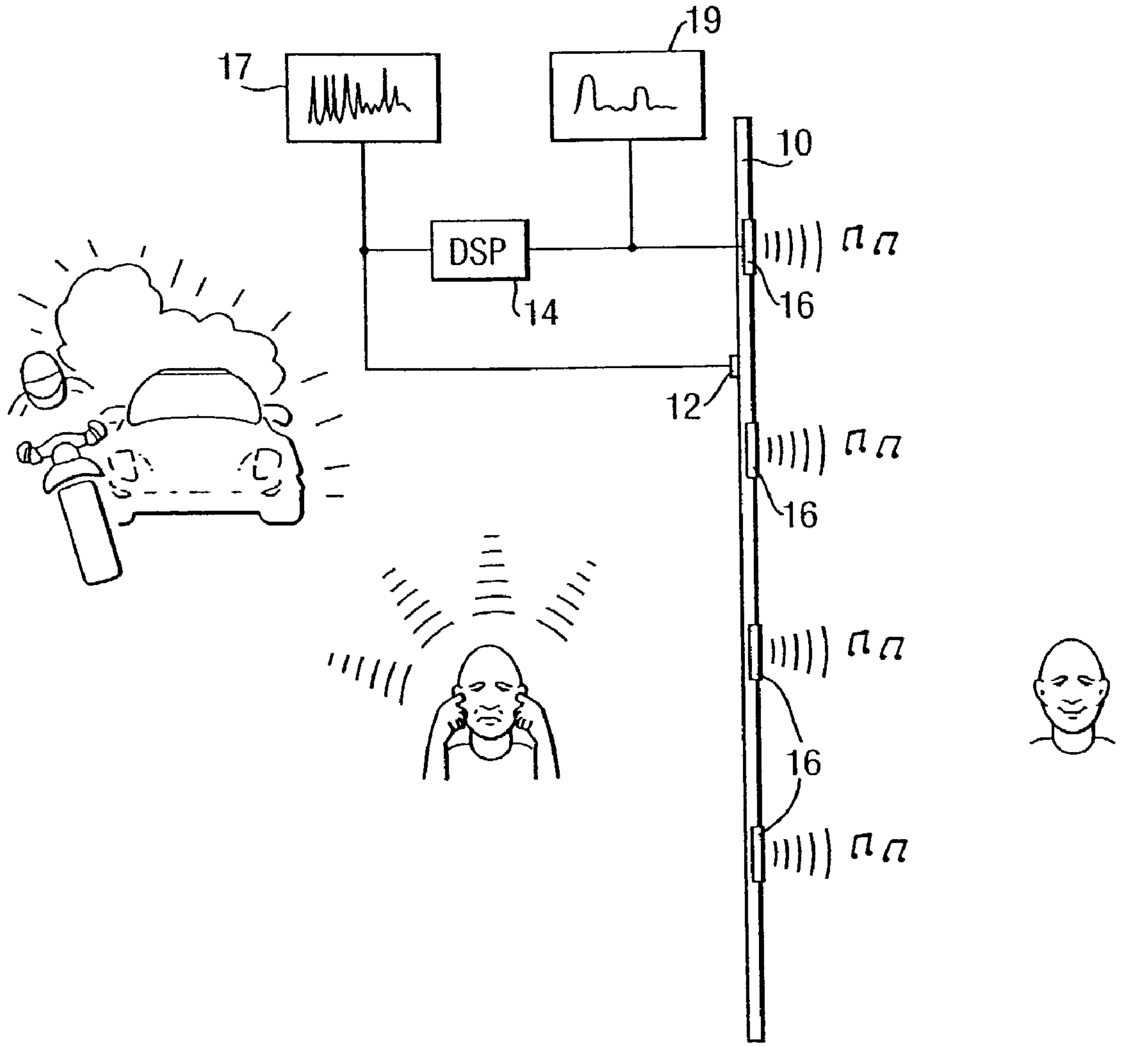
FIG. 2 is a schematic diagram of an embodiment of the invention.

An embodiment of the present invention will now be described with reference to FIGS. 2 to 18. As shown in FIG. 2, in this embodiment, the microphones 12 and the loudspeakers 16 are both mounted on the curtain 10 itself. Otherwise this embodiment is as described in relation to FIG. 1, like parts being designated by the same reference numerals.

The DSP 14 serves to analyze the electrical signals supplied from the microphones 12 and in response to such analyzed signals to generate sound signals for driving the loudspeakers 16. For this purpose, the DSP 14 employs an algorithm, described below with reference to FIGS. 3 to 18.

Figure 3:
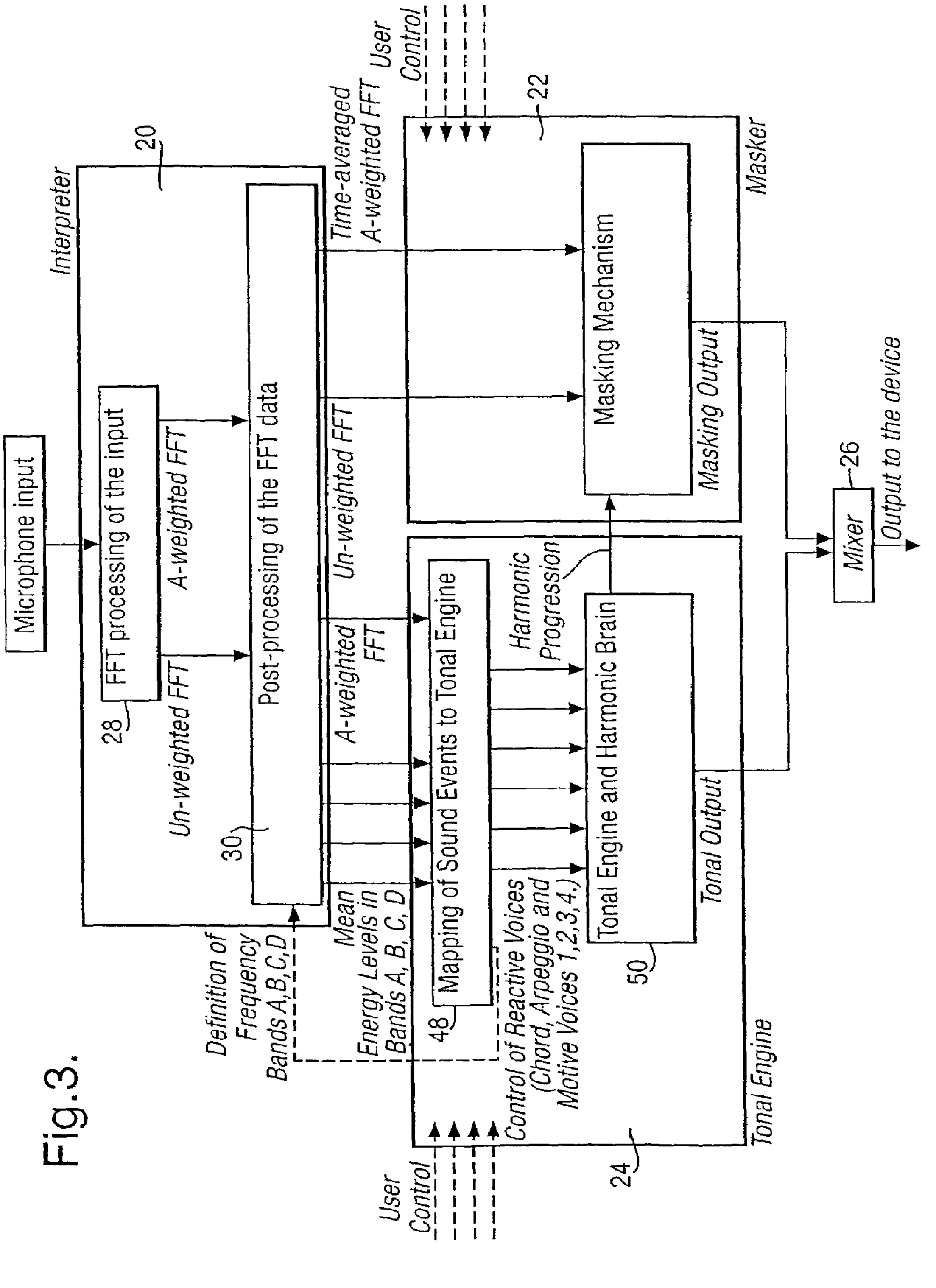
FIG. 3 is a schematic block diagram of a signal processor of FIG. 1 or 2 for performing an algorithm according to the present invention.
Figure 4:
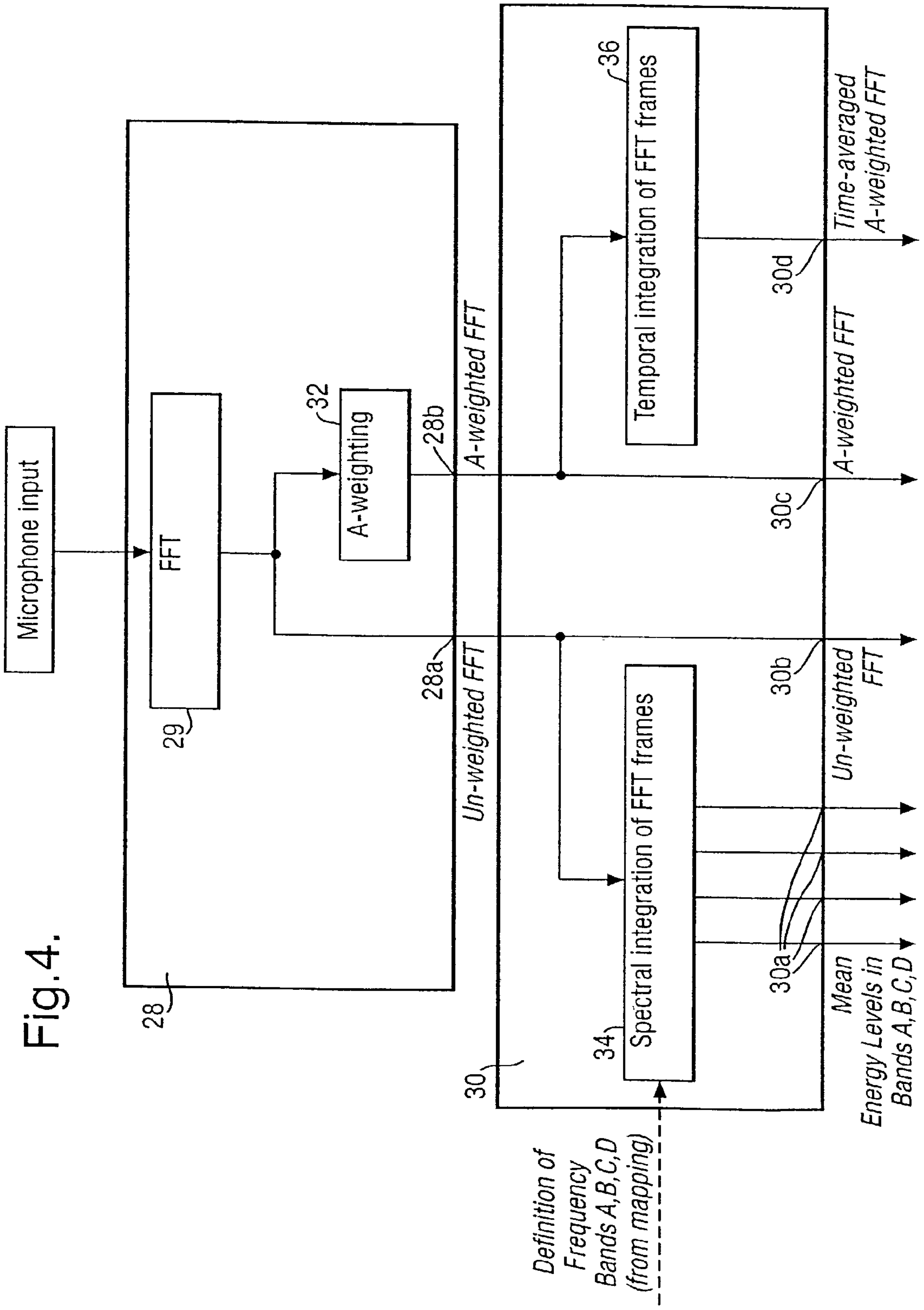
FIG. 4 is a block diagram of an interpreter of the processor of FIG. 3.

FIG. 3 is a schematic block diagram of the processor within the DSP 14, which effectively comprises three blocks, each for performing a respective sub-routine or sub-routines of the algorithm. More especially, the DSP 14 comprises an interpreter 20 arranged to receive as input noise signals from the microphones 12 and to perform an analysis of the characteristics of these signals for generating data analysis signals as outputs. These data analysis signals are supplied to a masking arrangement 22 on the one hand and to a tonal engine 24 on the other hand. The masking arrangement 22 responds to the data analysis signals by generating a set of related sound signals of different frequencies which are mixed for supplying the masker output. The tonal engine 24 responds to the data analysis signals by generating tonal sequence signals as output. The outputs of the masking arrangement 22 and the tonal engine 24 are then mixed in a mixer 26 to generate an output sound signal for supply to the loudspeakers 16.

As shown in FIG. 3, the interpreter 20 comprises a fast Fourier transform processor 28 for receiving the input signals from the microphones 12, and an integration arrangement 30 responsive to outputs from the Fourier transform processor 28 to generate data analysis signals for output from the interpreter 20. The Fourier transform processor 28 and the integration arrangement 30 are shown in greater detail in FIG. 4.

More especially, the Fourier transform processor 28 includes a detection circuit 29 that responds to the input signals from the microphones 12 by detecting the frequencies and amplitudes of the input signals and generating corresponding frequency-amplitude data. These signals are passed on the one hand directly as unweighted Fourier transform signals to an output 28*a* of the Fourier transform processor 28. They are also passed by way of a weighting arrangement 32 to provide weighted Fourier transform signals at another output 28*b* to the Fourier transform processor 28. The weighting arrangement 32 is designed to adjust the input frequencies to take account of the non-linearity of the human auditory system. For example, the weighting arrangement 32 may employ an A-weighting or other function to approximate respective listening perception models.

In the integration arrangement 30, the unweighted Fourier transform signals are passed firstly by way of a spectral integrator 34 to a first output 30*a* of the integration arrangement 30 and secondly directly to a second output 30*b* of the integration arrangement 30. The spectral integrator 34 divides the frequency range of the incoming Fourier transform signals into four bands A, B, C and D and then averages the amplitudes of the signals within each of these four bands. The four bands are selected by an output from the tonal engine 24 to be described later. The weighted Fourier transform signals are passed in the integration arrangement 30 firstly direct to a third output 30*c* and secondly by way of a temporal integrator 36 to a fourth output 30*d*. The temporal integrator 36 sets a temporal window constituting a plurality N of the Fourier transform time frames and then averages the Fourier transform signals received during each successive set of N time frames. The signals from the first and second outputs 30*a*, 30*b* of the integration arrangement 30 are supplied to the tonal engine 24, while the signals from the third and fourth outputs 30*c*, 30*d* are supplied to the masking arrangement 22.

Figure 5:
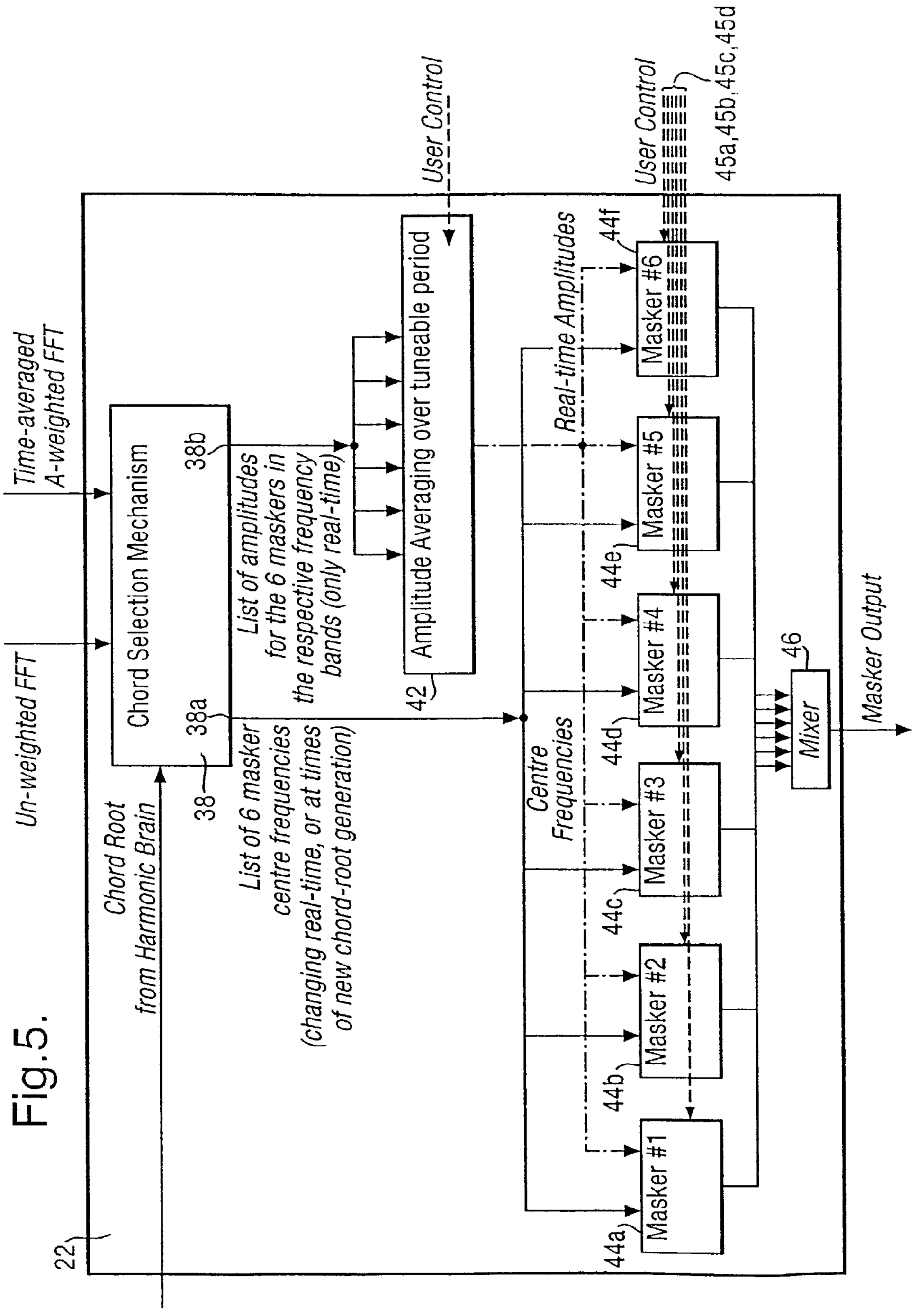
FIG. 5 is a block diagram of a masking arrangement of the processor of FIG. 3.
Figure 6:
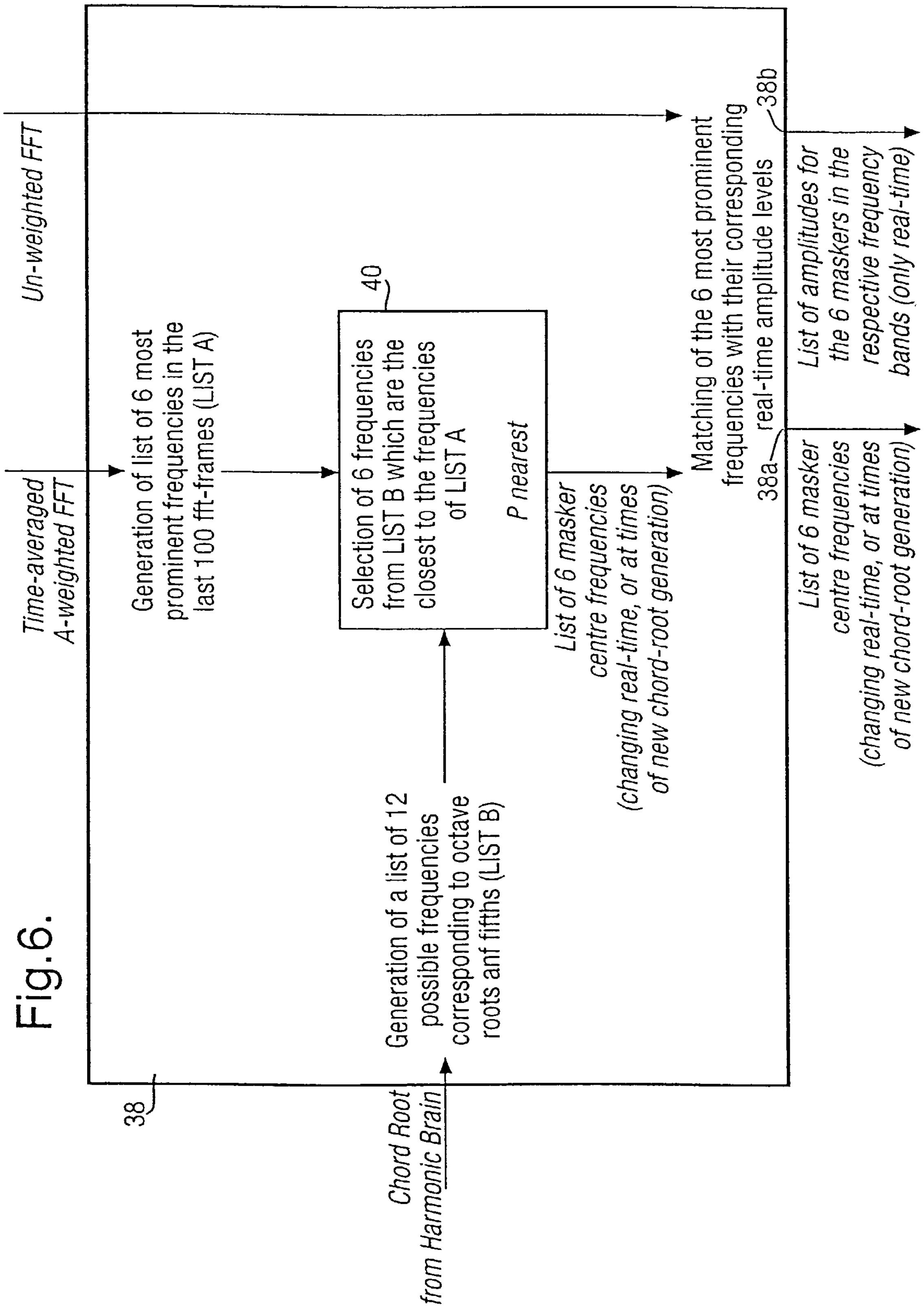
FIG. 6 is a block diagram of a chord selection mechanism of the masking arrangement of FIG. 5.
Figure 7A:
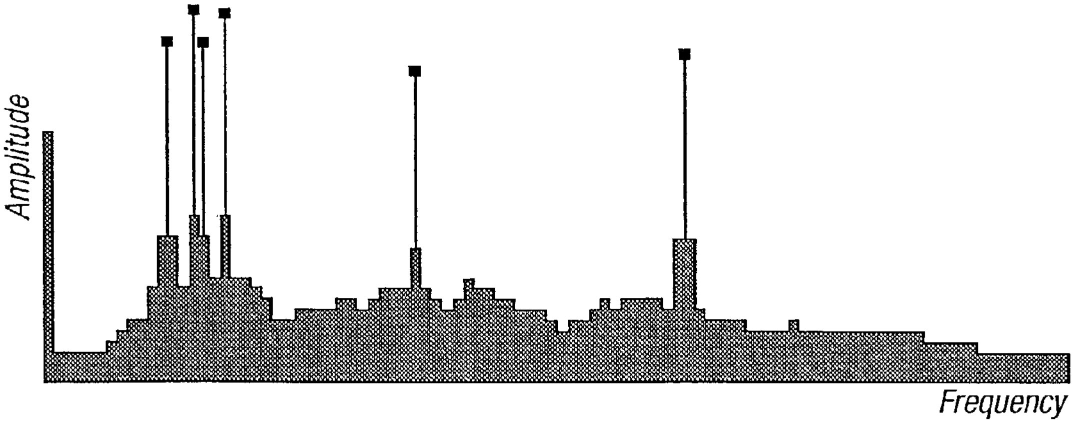
FIGS. 7(*a*)–(*c*) are signal diagrams representing operation of the masking arrangement of FIG. 5.
Figure 7B:
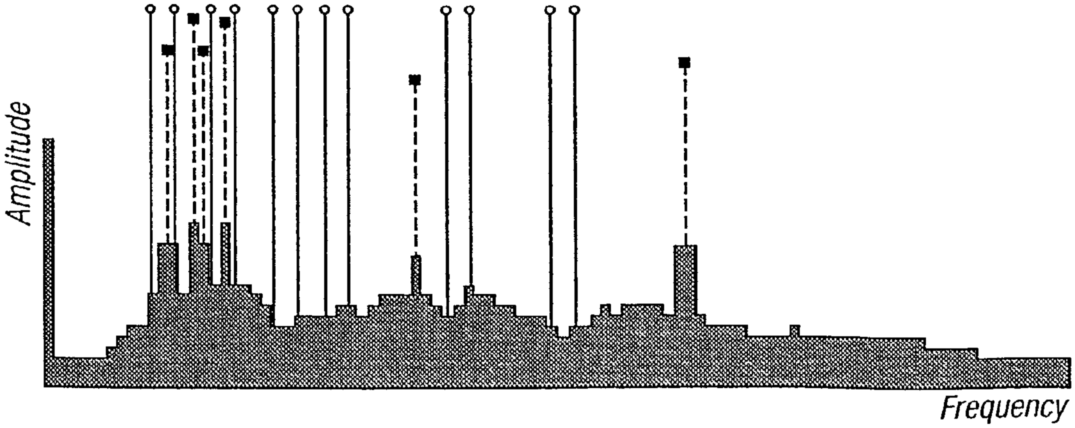
Figure 7C:
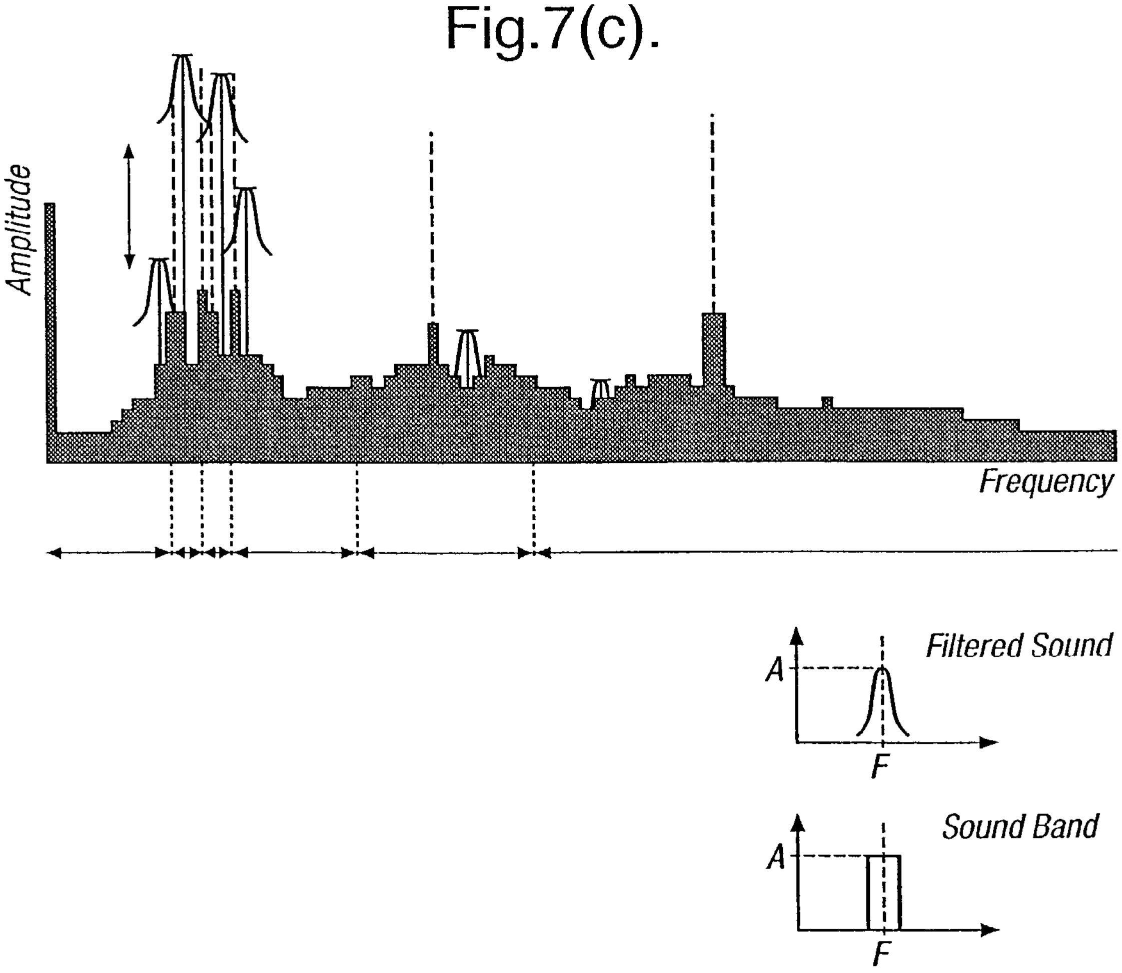

Turning to FIG. 5, the masking arrangement 22 features a chord selection mechanism 38, which is shown in greater detail in FIG. 6. This chord selection mechanism 38 monitors the time averaged signals received from the fourth output 30*d* of the integration arrangement 30 and outputs a number S, for example 6, of the most prominent frequencies appearing in the time averaged signal of the last N, for example 100, time frames for use in generation of the masker output. FIG. 7(*a*) shows an example of the time averaged signals received by the chord selection mechanism 38, in which the six most prominent frequencies are indicated by black squares. These six most prominent frequencies, designated list A, are then compared in a selection device 40 with twelve possible frequencies, designated list B, which are generated in response to signals from the tonal engine 24 as described below and which correspond, for example, to octave roots and fifths. FIG. 7(*b*) shows marked as white circles the twelve possible frequencies of list B against the six frequencies of list A. The selection device 40 selects out of list B the six frequencies corresponding most closely to the six frequencies of list A as center frequencies for future processing and supplies output signals corresponding to these six center frequencies. The chord selection mechanism 38 then matches the six center frequencies with their corresponding real-time amplitude levels determined from the unweighted Fourier transform signals, and generates at a first output 38*a* signals representing a list of the six center frequencies and at a second output 38*b* signals representing a list of the corresponding amplitudes.

Turning back to FIG. 5, the signals representing the list of six amplitudes are supplied to an amplitude averager 42 which performs amplitude averaging on each of the six amplitudes over a period of time frames set by the user. The amplitude averager 42 generates six outputs for supply respectively to six tone generators 44*a* to 44*f* Each of the tone generators 44 also receives as input a respective one of the signals representing the six center frequencies supplied by the chord selection mechanism 38.

The tone generators 44 process respectively each center frequency signal and the corresponding averaged amplitude signal according to a control input determined by the user in order to generate a corresponding output. There are four possible control inputs 45*a* to 45*d* for setting the output from each tone generator 44 to correspond respectively to:

(i) a noise band (45*a*)

(ii) sound based on a given sample (45*b*)

(iii) filtered noise (45*c*)

(iv) sound created by a library of musical sound (45*d*).

The user has the option of selecting just one from the four control inputs 45*a* to 45*d* or a combination of any of the four control inputs to apply the same to all of the tone generators 44. It is to be appreciated that "noise" here means randomly generated sound. The control input from the user together with the outputs from the amplitude averager 42 and the chord selection mechanism 38 then determine the output from each tone generator 44. FIG. 7(*c*) gives examples of a noise band and filtered noise, and also shows the outputs of the tone generators 44 when a control input for filtered noise has been selected. In the case of sound based on a sample or sound created by a library of musical sound, it will be appreciated that the signal waveform will be much more complex.

Figure 14:
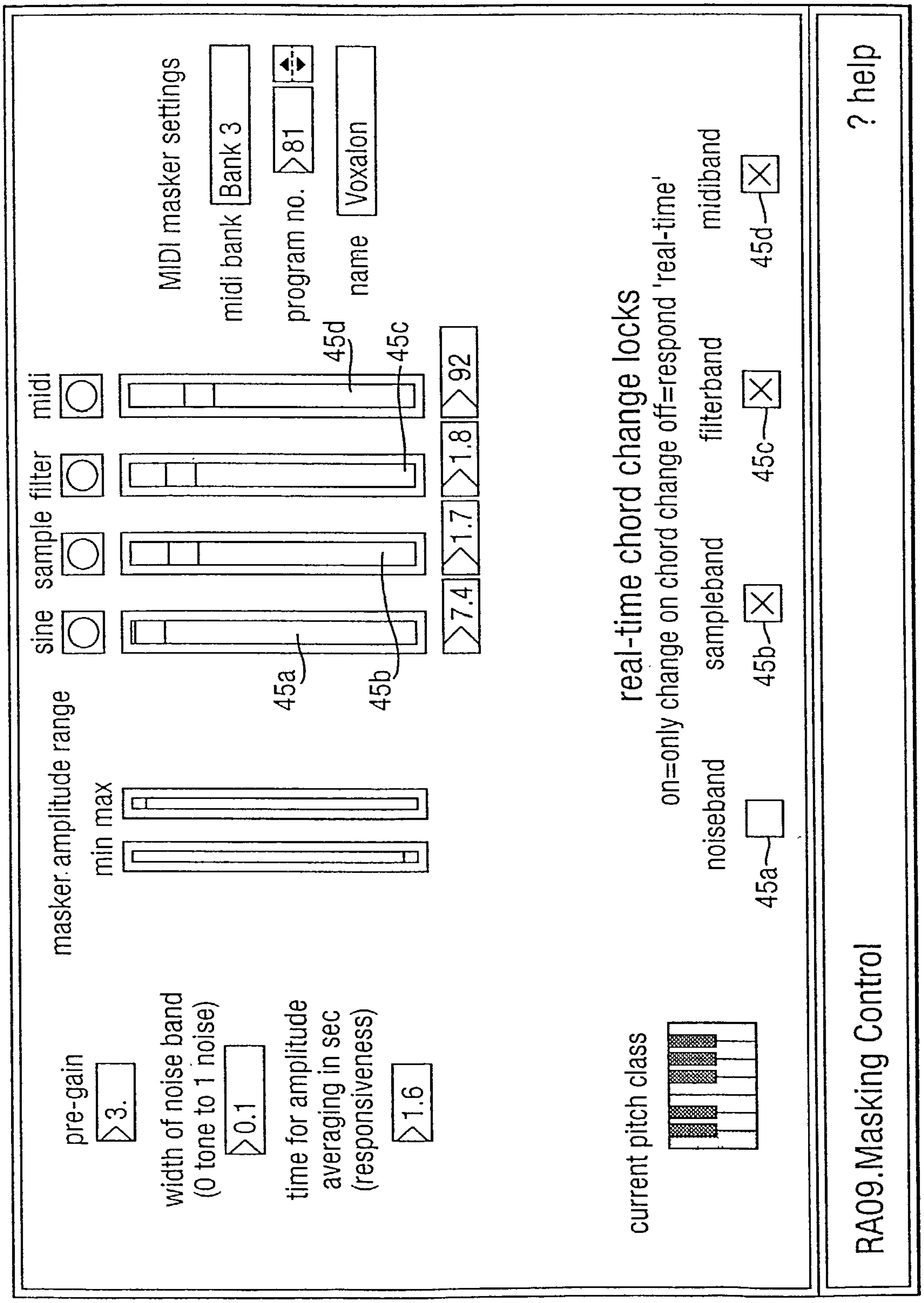
FIG. 14 is a view of a user adjustable display on a PC screen for inputting control functions to the masking arrangement of FIG. 5.

FIG. 14 shows, by way of example, a display available on a screen of the DSP 14 on which the possible control inputs 45*a* to 45*d* are shown and may be selected and variably set, for example by means of a mouse.

The outputs from all of the tone generators 44 are supplied to a mixer 46 for generating a master output from the masking arrangement 22.

Figure 8:
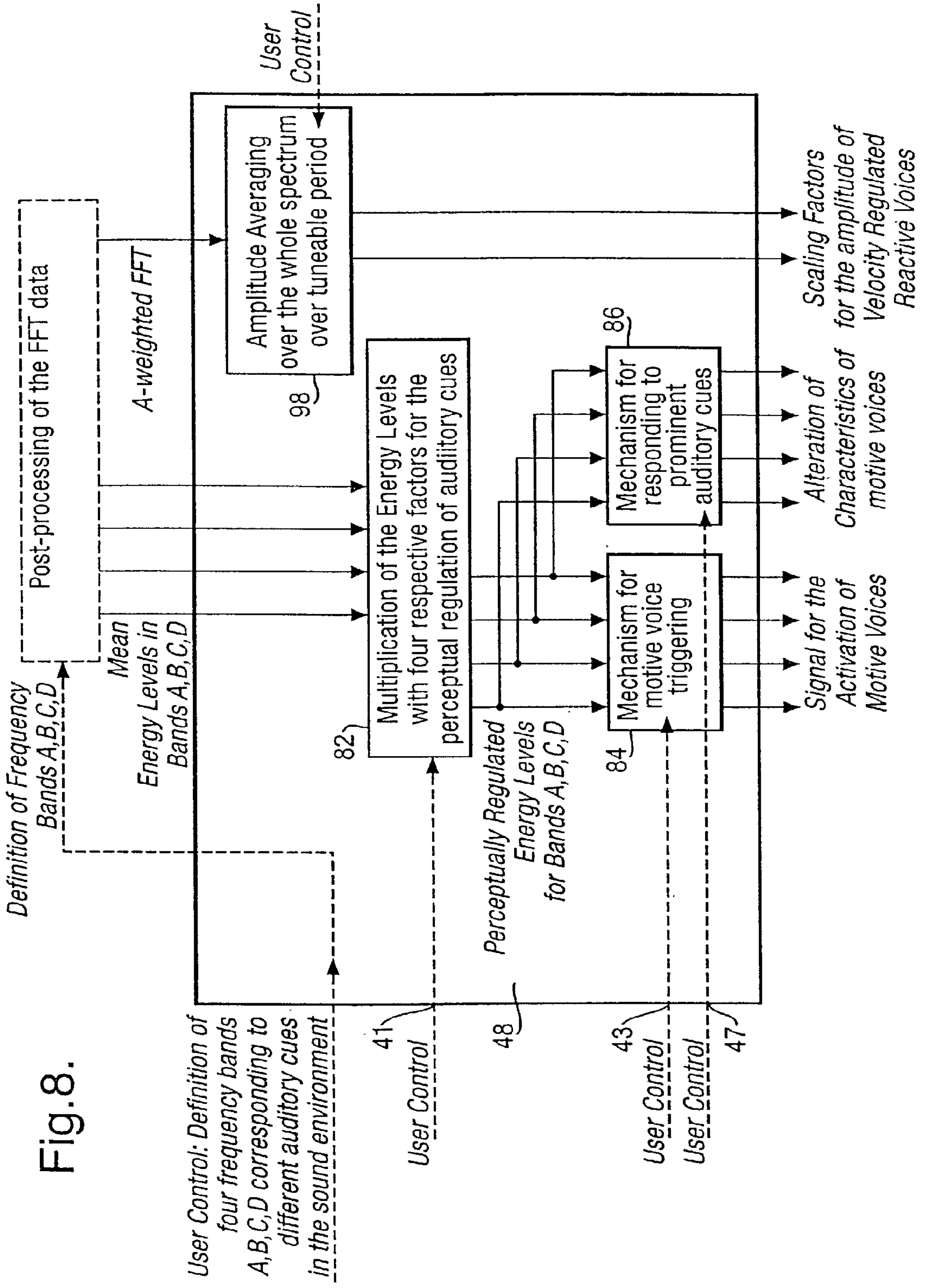
FIG. 8 is a block diagram of a mapping device of a tonal engine of the processor of FIG. 3.
Figure 11:
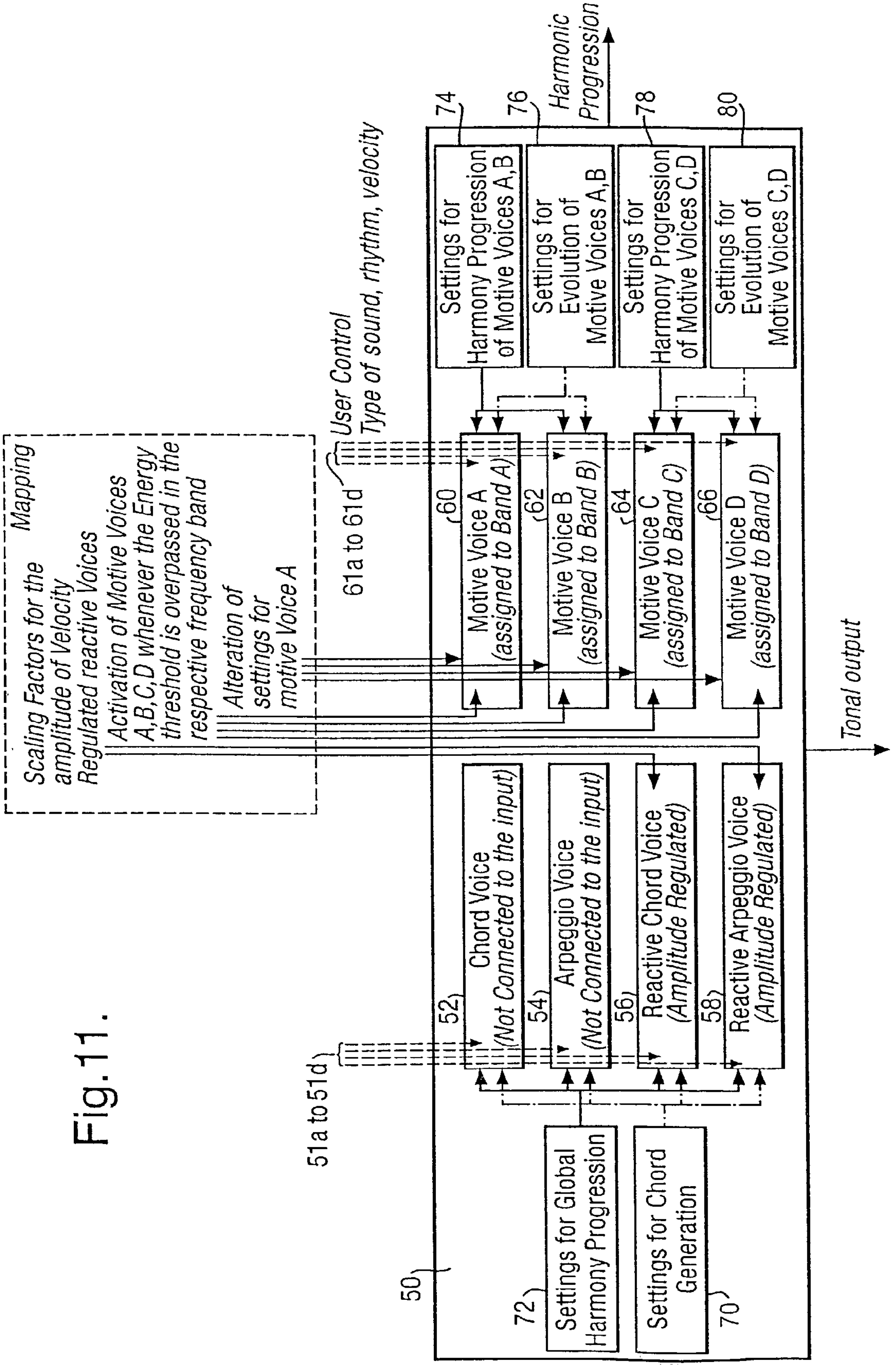
FIG. 11 is a block diagram of a harmonic sound generator of the tonal engine of the processor of FIG. 3.
Figure 12:
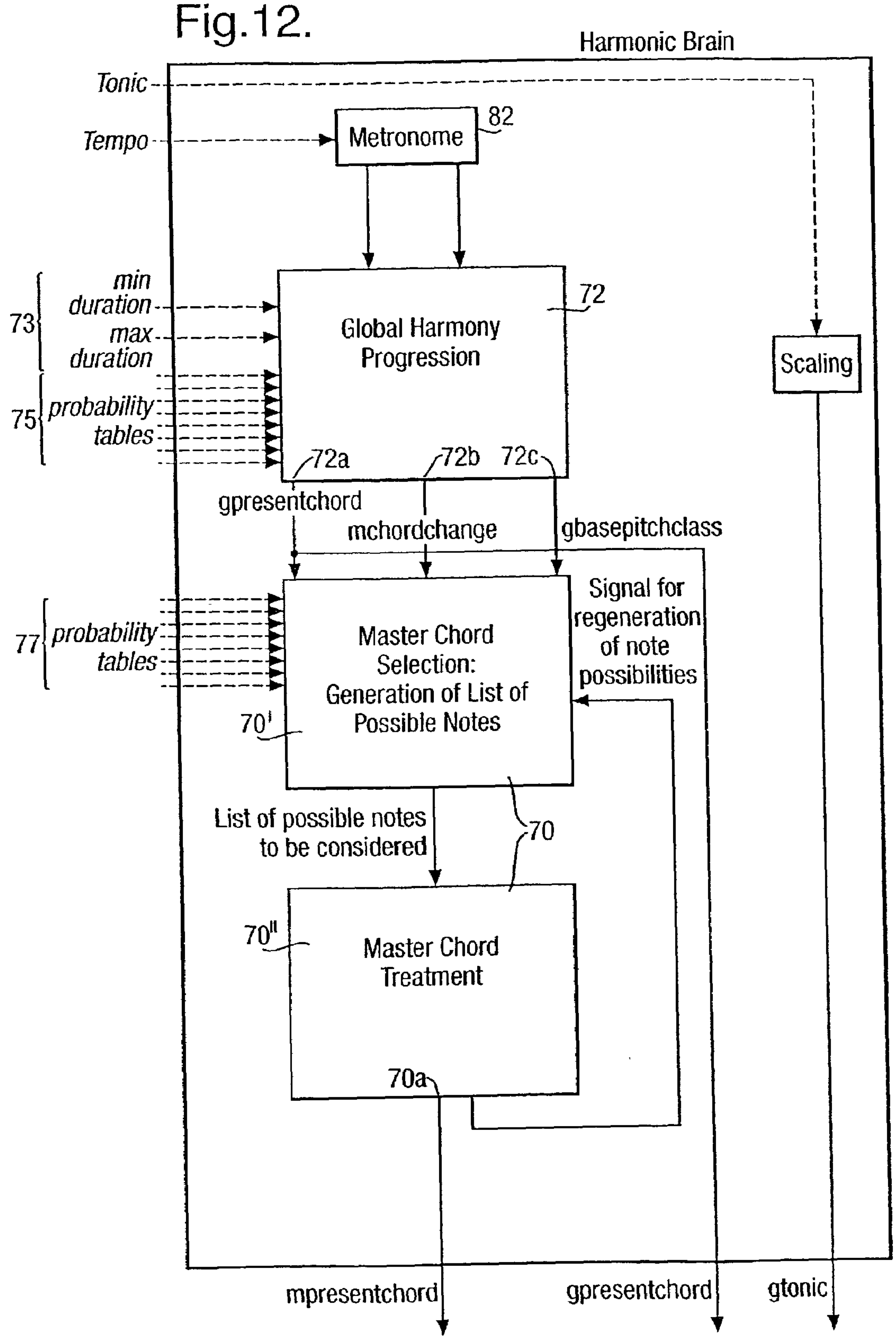
FIGS. 12 and 13 are more detailed block diagrams of the harmonic sound generator of FIG. 11.
Figure 13A:
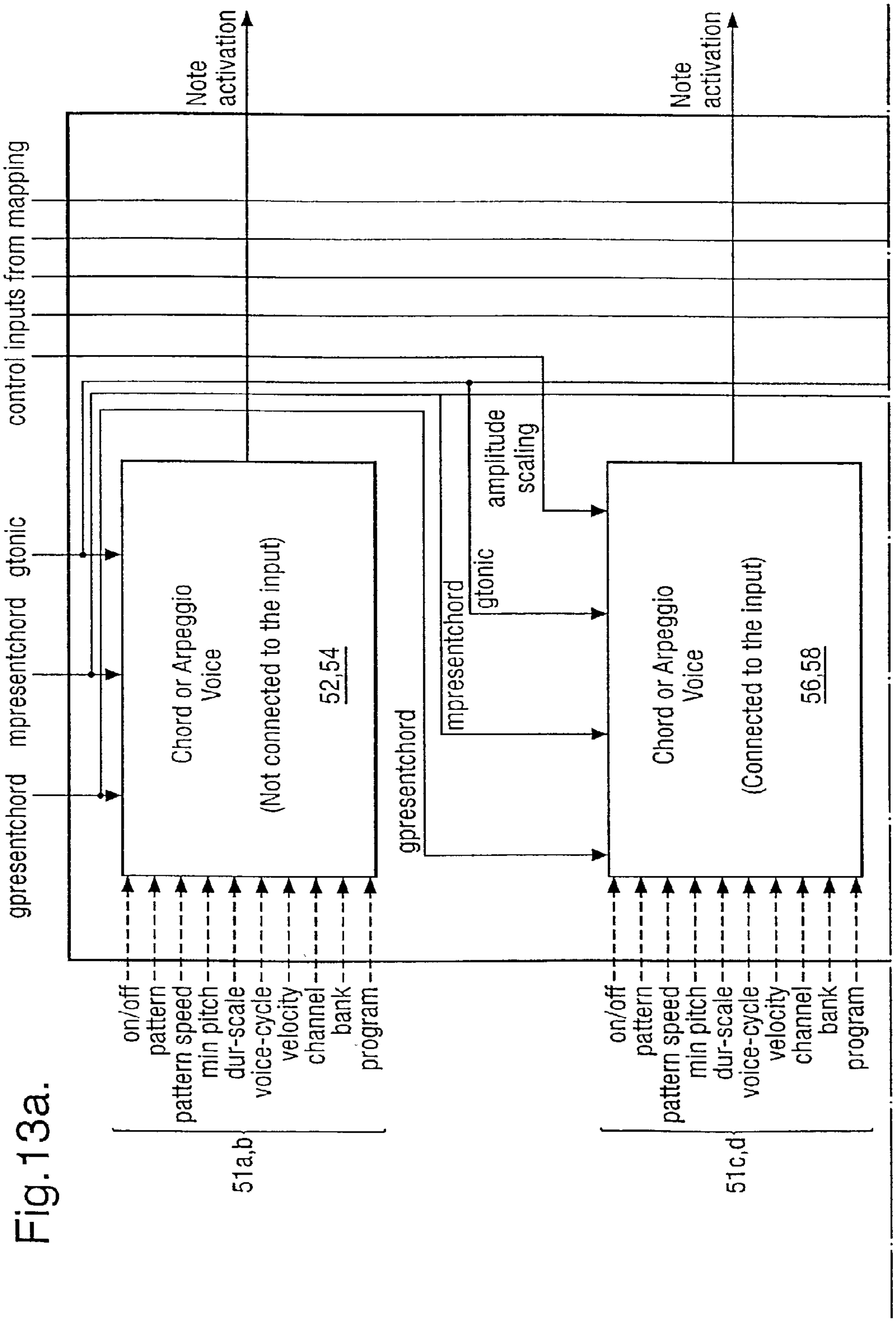
Figure 13A:
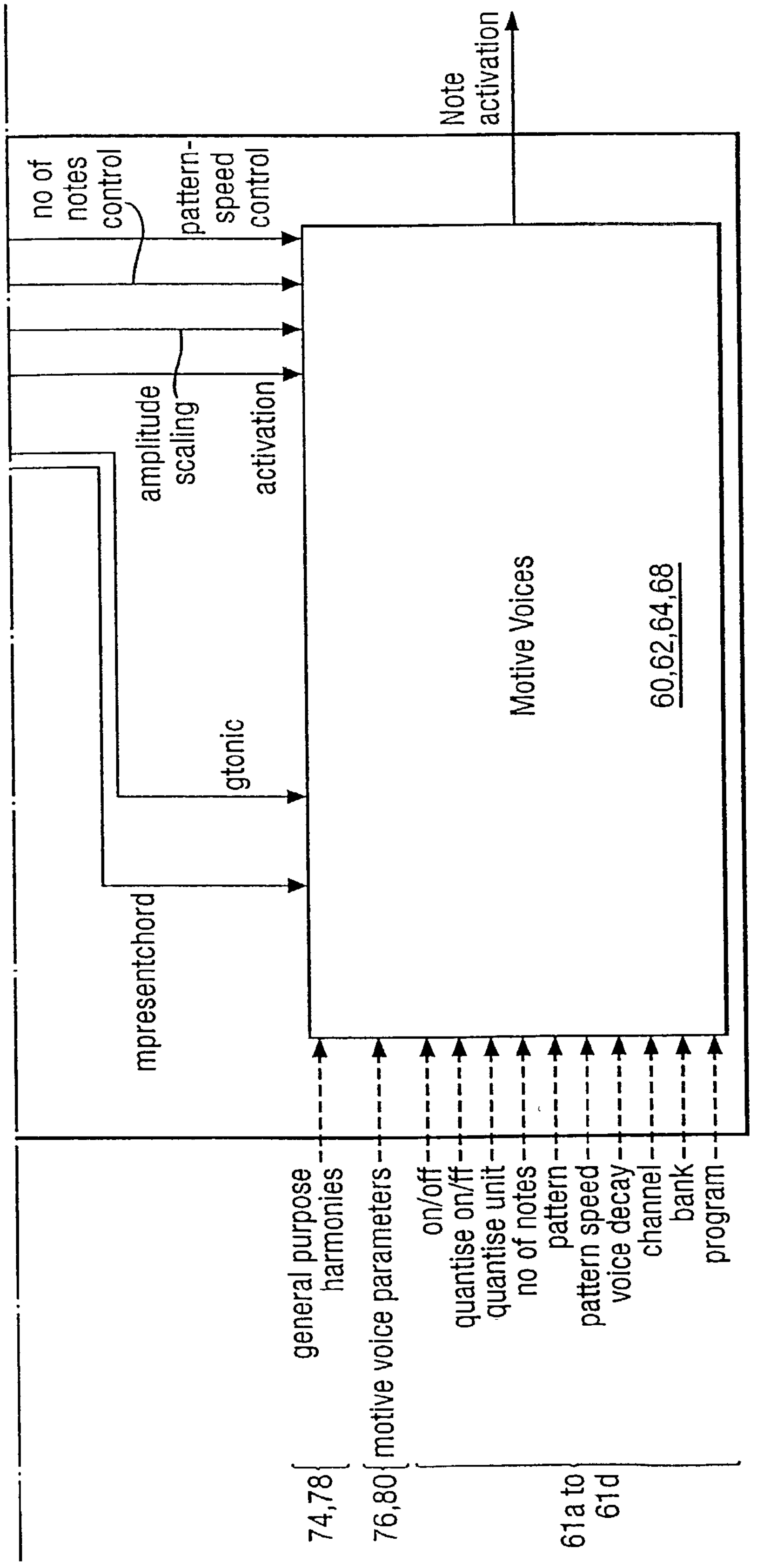
Figure 13B:
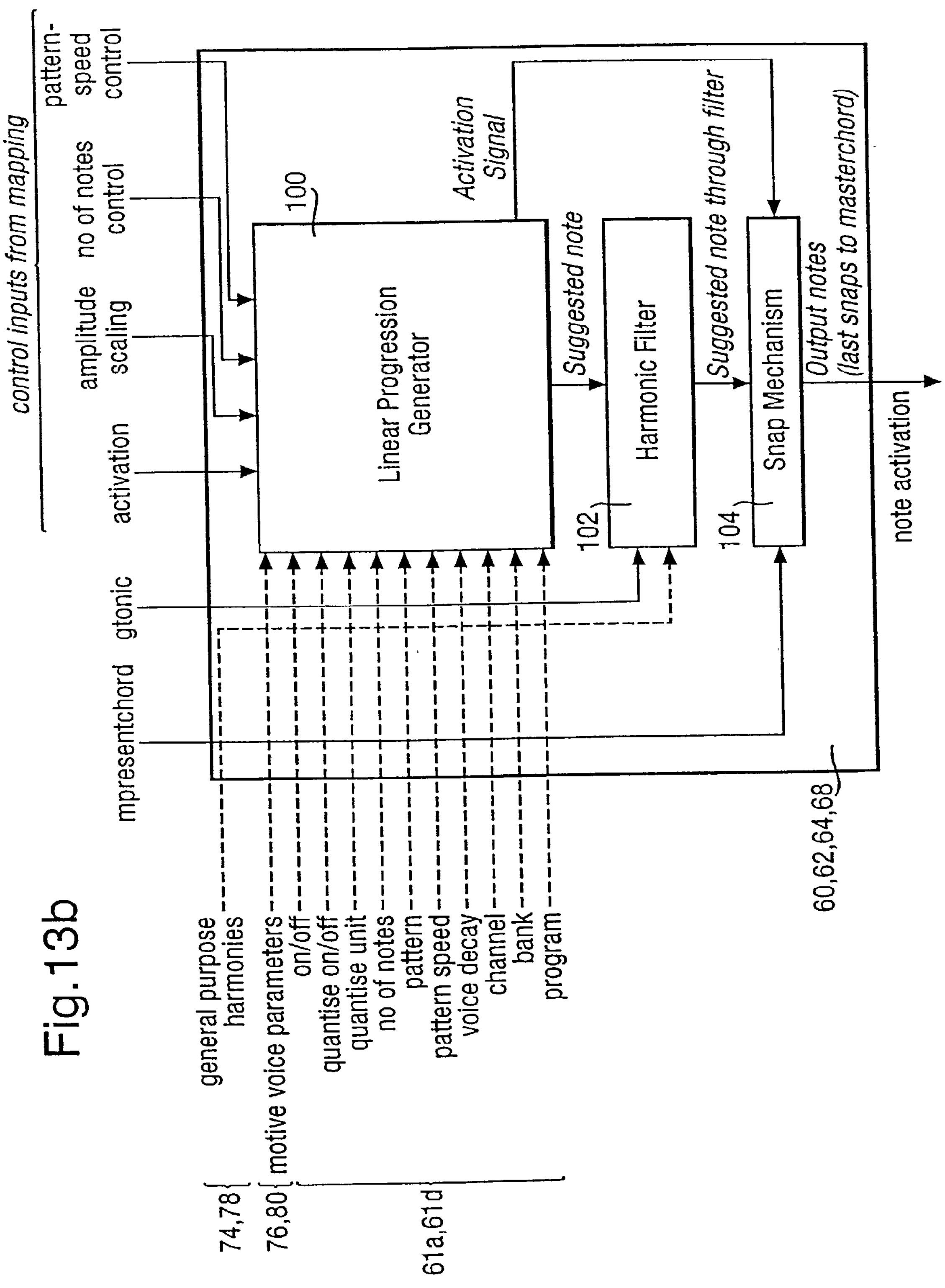

Turning now to FIGS. 3, 8, 11 to 13 and 15 to 18, the tonal engine 24 comprises a mapping device 48 responsive to the signals from the first output 30*a* of the interpreter 20 to generate control signals, and a tonal sequence generator 50 responsive to the control signals from the mapping device 48 to supply an output from the tonal engine 24. The mapping device 48 is illustrated in FIG. 8, and the tonal sequence generator 50 is illustrated in FIGS. 11 to 13. The tonal sequence generator 50 will be described first.

As shown in FIG. 11, the tonal sequence generator 50 comprises eight voice generators 52, 54, 56, 58, 60, 62, 64 and 66 for generating signals representing tonal sequences in dependence firstly on user inputs 51*a* to 51*d* and 61*a* to 61*d* respectively and secondly upon the inputs received from the mapping device 48. The voice generators 52 and 54 are arranged respectively to generate signals representing musical chords and arpeggios. These voice generators are responsive only to user inputs 51$a$ and 51$b$ but not to signals from the mapping device 48. Voice generators 56 and 58 are also arranged to produce signals representing musical chords and arpeggios, but on this occasion they are responsive both to user inputs 51$c$ and 51$d$ and to signals from the mapping device 48. Voice generators 60 to 66 each generate signals representing sequences of tones determined according to user inputs 61$a$ to 61$d$ as modified by inputs received from the mapping device 48.

More particularly, the user applies inputs to all eight of the voice generators 52 to 66 to determine the type of sound, for example flute or piano, the rhythm and the sound velocity required. The user is also able to select inputs for programming settngs 70 and 72 for determining the musical key and harmony progression respectively required for the chord and arpeggio voice generators 52 to 58. In addition, the user is able to select input settings 74 and 76 for determining respectively the harmony progression and evolution or constraints on sequential note selection respectively required for the voice generators 60 and 62. Finally, the user is able to select input settings 78 and 80 each corresponding to the setting 74 and 76 but for controlling the voice generators 64 and 66.

The setting circuits 70 to 80 and the voice generators 52 to 68 are further illustrated in FIGS. 12 and 13. As shown in FIG. 12, and referring firstly to the setting circuits 70 and 72, these receive timing signals from a clock circuit 82. The setting circuit 72 for harmony progression is arranged to receive inputs 73 representing the minimum and maximum duration in beats for the voice to remain at a certain pitch class, if chosen. The setting circuit 72 is also arranged to receive a user input 75 in the form of probability scales or tables representing a "harmonic base" setting. The setting circuit 72 computes from these inputs 73, 75 three outputs 72$a$, 72$b$ and 72$c$ as follows: The output 72$a$ is a signal designated "gpresentchord" in the form of a number representing the pitch class of the base of the chord. The output 72$b$ is a signal designated "mchordchange" which initiates a chord selection. The output 72$c$ is a signal designated "gbasepitchclass" representing the pitch class offset by a user input tonic. These three signals are all supplied to a master chord selection circuit 70' of the setting circuit 70, while the signal "gpresentchord" is also supplied to each of the voice generators 52 to 58.

The setting circuit 70 comprises the master chord selection circuit 70' for generating a list of possible notes for output and a master chord treatment circuit 70" for generating a control signal at an output 70$a$. The master chord selection circuit 70' is arranged to receive a user input 77 in the form of activation signals for activating the master chord selecting circuit and an input 77$b$ in the form of probability scales or tables for providing a basis for the selection of possible notes for overall output. The masterchord selection 70' then computes a list of possible notes for consideration for output by the tonal engine 50 and supplies these to the master chord treatment circuit 70". This master chord treatment circuit 70" evaluates the musical feasibility of this combination of notes, for example, by determining whether they all relate to just one of a major or a minor musical key, and either supplies a signal representing this combination of notes at the output 70$a$ or provides a feedback signal to the master chord selection circuit 70' to enable that circuit to generate a new list of possible notes to be considered. The output supplied by the master chord treatment circuit 70" at the output 70$a$ is a signal designated "mpresentchord" representing the master chord setting, which is supplied to all of the voice generators 52 to 58.

Turning now to FIG. 13, the various inputs to the voice generators 52 to 58 are illustrated, showing the user inputs 51$a$ to 51$d$ as well as the input signals "gpresentchord" from the setting circuit 72 and the signal "mpresentchord" from the setting circuit 70. In addition, the voice generators 52 to 58 receive a signal "gtonic" representing a user input tonic, and the voice generators 56 and 58 receive a scaling input signal from the mapping device 48.

Figure 16:
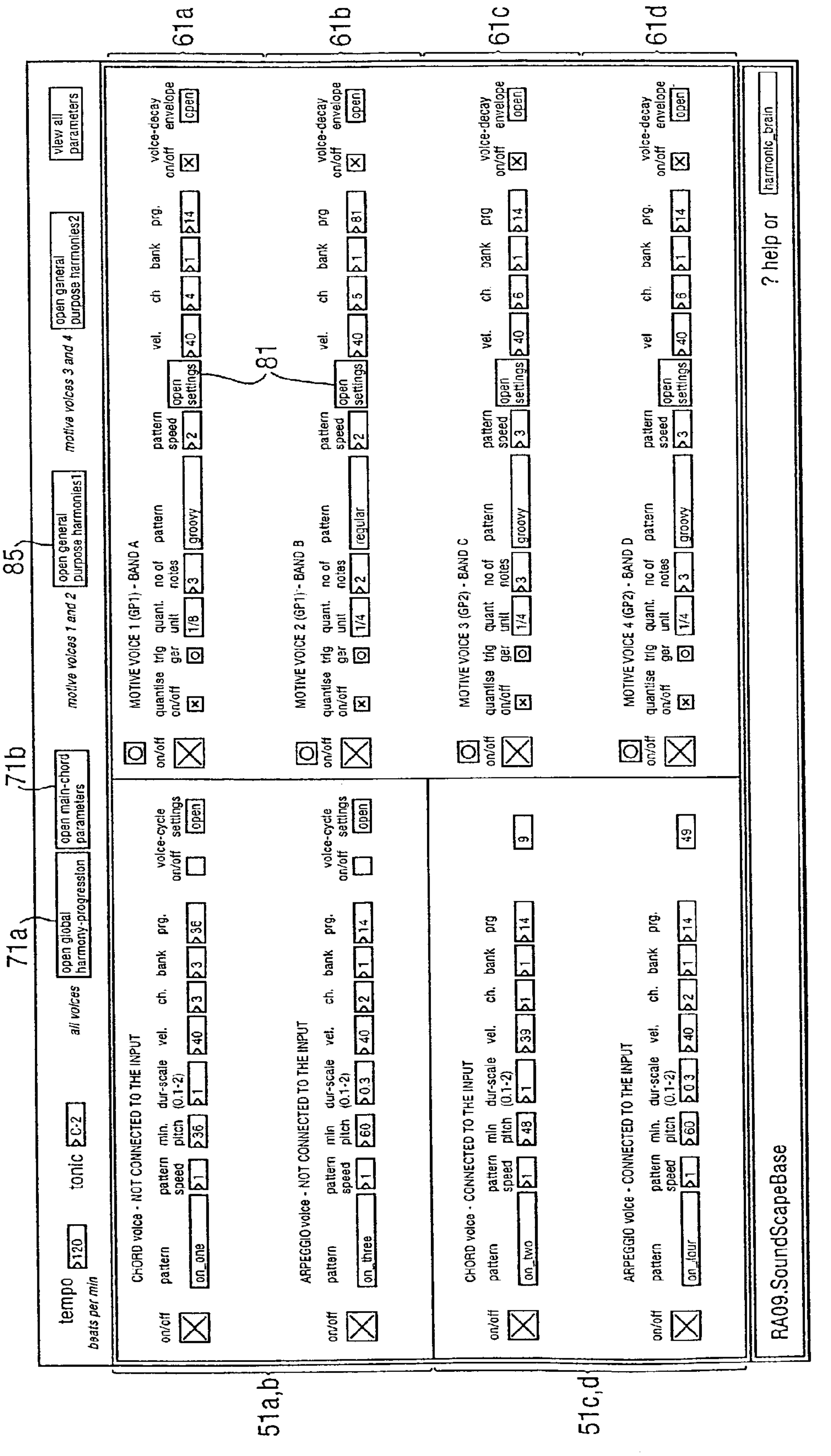
FIGS. 16 to 18 are views of user adjustable displays for inputting control functions to the harmonic sound generator of FIG. 11.
Figure 17:
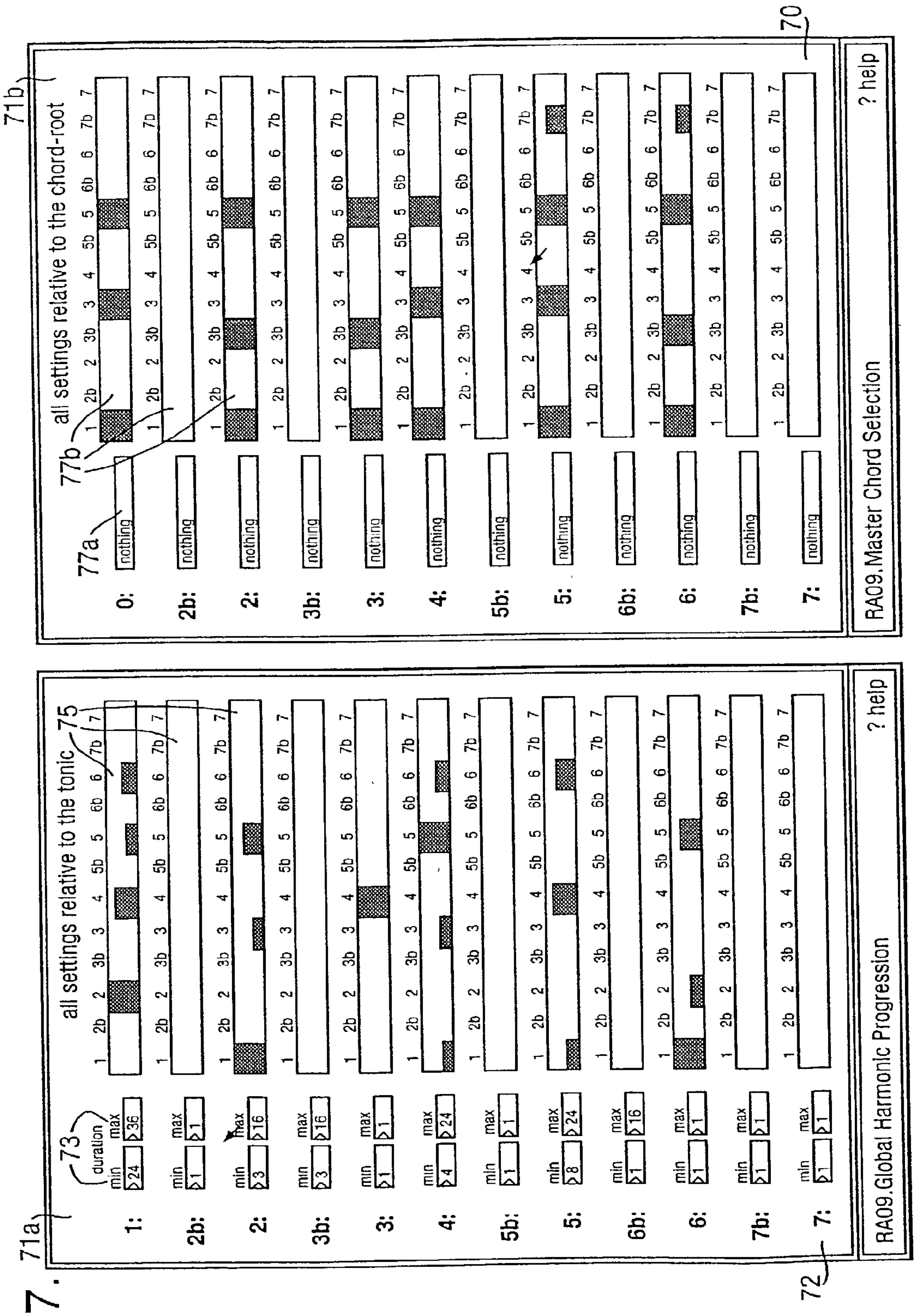

FIGS. 16 and 17 show, by way of example, displays available on the screen of DSP 14 on which the possible user inputs 51$a$ to 51$d$ and 73, 75 and 77 are indicated and may be selected and variably set, for example, by way of a mouse.

FIG. 16 shows a screen window displaying the user inputs 51$a$ to 51$d$, as follows:

PATTERN: selects the type of pattern to use. Available settings are 'very regular', 'regular', 'chaotic', 'groovy' and 'dense'.

PATTERN SPEED: determines the density of the pattern, the number of notes per bar (1=least, 6=most dense).

MIN. PITCH: selects the minimum pitch to be output.

DURATION-SCALE (0.1–2.0): scales the duration of the notes (2.0 results in notes double the length of those at 1.0. Values above 1.0 lead to overlap with the following notes. Possible values: 0.1–2.0).

VEL.: selects the velocity of the midi-output

CH.: selects the channel of the midi-output

BANK: selects a bank of synthesizers to use.

PRG: selects the program to use.

FIG. 16 also shows selection indicators 71$a$ and 71$b$ for accessing screen windows shown in FIG. 17 for providing the user inputs 73, 75, 77$a$ and 77$b$. As shown in FIG. 17, the min/max user settings 73 may be set as numbers to determine the range of possible durations (in beats) for the voice generated to remain at the certain pitch class, if chosen. The settings 75 are shown as a series of multi-sliders on each of which a probability scale (1, 2b, 2 etc as shown) may be selected by the user. Bars of equal height represent equal probability for the selection of either 1, 2b etc. The setting 77$a$ selects a note output possibility from a list of pre-programmed note combinations (major-triad, minor-triad, major, minor, pentatonic, chromatic etc.), and the setting 77$b$ comprises a further series of multi-sliders on each of which the user can set a probability scale (1, 2b, 2 etc as shown) as before. The user selects one of the settings 77$a$, 77$b$ only.

Turning now to FIGS. 11, 13$a$ and 13$b$, the settings 74 to 80, the user inputs 61$a$ to 61$d$ and the circuit construction of each of the voice generators 60 to 68 will now be described.

As shown in FIG. 13$a$ and 13$b$, the settings 74, 78 representing general purpose harmonies and the settings 76, 80 representing motive voice parameters are supplied to the voice generators 60 to 68, along with the user inputs 61$a$ to 61$d$ and the signal "gtonic", the signal "mpresentchord" from the master chord treatment circuit 70", and the inputs from the mapping device 48.

Each of the motive voice generators 60 to 66 employs a linear progression generator 100, which creates a note suggestion based on a melodic progression using the settings 76, 80 and the user inputs 61$a$ to 61$d$. An output representing the suggested note is then supplied by the linear progression generator 100 to a harmonic filter 102, which decides whether the note is to be filtered out or not depending on the settings 74, 78. If not, the harmonic filter supplies an output to a snap mechanism 104, which is activated by a signal from the linear progression generator 100 as it supplies the last note of a particular sequence and which responds by snapping the note to the master chord represented by the signal "mpresentchord" to ensure musical coherence.

Figure 18:
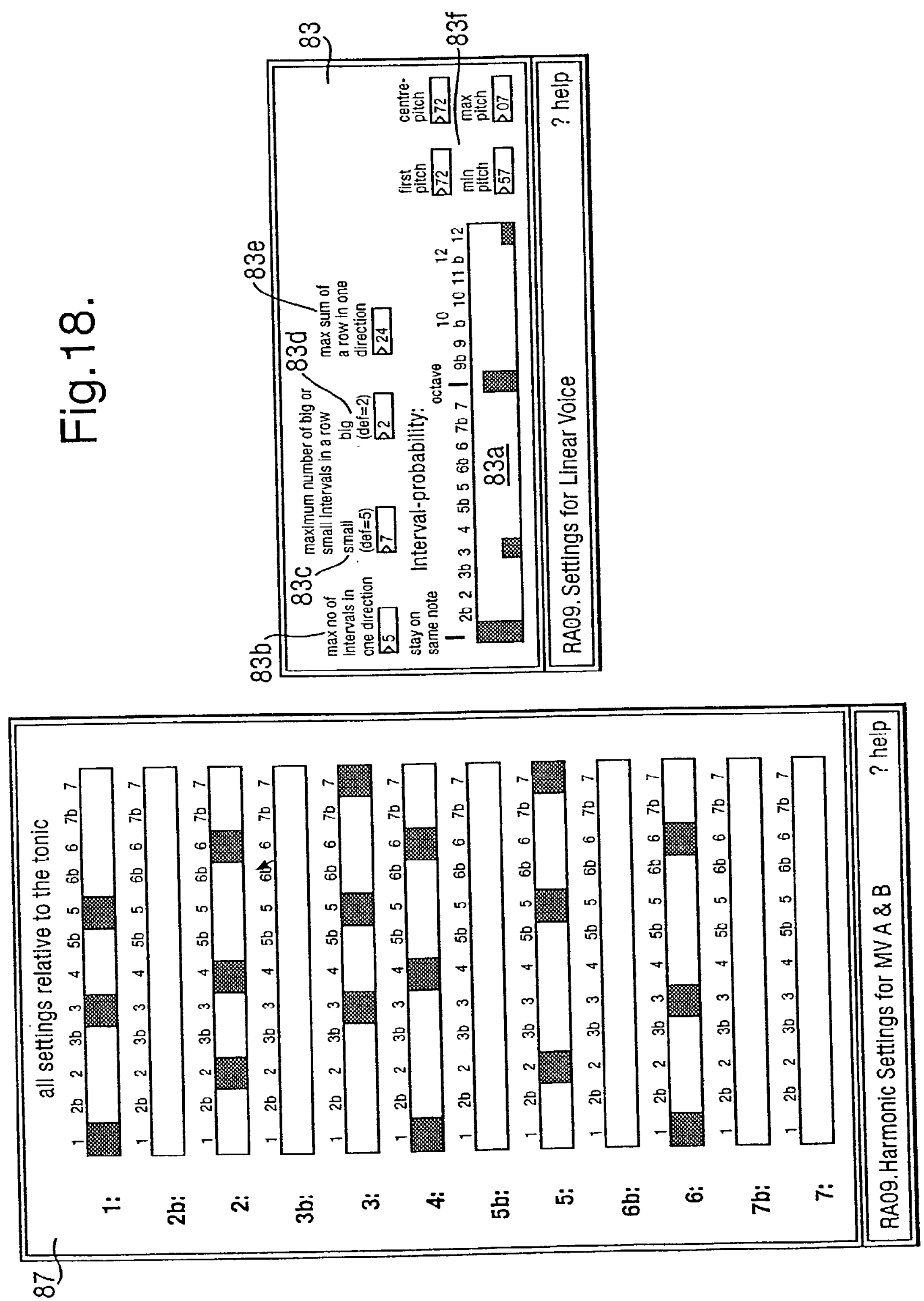

The settings for controlling the linear progression generator 100 and the harmonic filter 102 are illustrated further in FIGS. 16 and 18. These FIGS. show, by way of example, displays available on the screen of the DSP 14 on which the possible user inputs 61*a* to 61*d* are indicated and may be selected and variably set, for example by way of a mouse, as well as a series of inputs 87 representing the settings 76, 80 accessed by way of a window setting 81 on the screen and a further series of inputs 83 representing the inputs 74, 78 accessed by way of a window setting 85 on the screen. As shown, the inputs 87 comprise a series of multi sliders on which the user can set a probability scale or table for selecting a current chord, while each of the inputs 83 includes a further multi slider for setting the evolution of the motive voices as indicated below.

As indicated above, each of the linear progression generators 100 creates a suggestion for a possible note based on a melodic progression using the probability scales 87, and the harmonic filter 102 determines whether this note is to be played using a weighted interval probability setting based on the inputs 83 to be set by the user by regulating two kinds of parameters: on the one hand, the user defines interval probability tables 83*a* (high or low probability to stay on the same note or move up to several tones higher), the maximum number 83*b* of intervals in one direction, the number of small intervals 83*c* in succession, the number of big intervals 83*d* in succession and the maximum sum of intervals 83*e* in any one direction allowed to be output by the motive voice generator. On the other hand, the user sets the minimum, maximum, first and center pitch 83*f*, in that way defining the frequency range of the tonal sequence. If the suggested note is enabled by the general purpose harmonies for the current pitch class, then the note is output by the motive voice generator. If not, then another note is suggested.

As shown in FIG. 16, the user inputs 61*a* to 61*d*, comprising the setting parameters for the motive-voices, may include:

QUANTIZE ON/OFF: selects whether quantization snaps the incoming triggers for activation of the respective motive voice to a rhythmic grid.

QUANT. UNIT: selects a unit of a quantization grid according to the tempo set in the control-panel.

CYCLE-DUR.: sets the duration of a fade-in/fade-out cycle of a motive voice in seconds. The fade-in/fade-out cycle scales the velocity of the voice by following an envelope contained in a table "voicecycle". By redrawing the table, the trajectory of the fade-in/fade-out cycle can be changed.

CYCLE ON/OFF: activates the cycle-function of a motive voice, if deactivated the voices play at the velocity set under velocity.

OPEN SETTINGS: opens the motive voice parameters 76 or 80 for the motive voice generators A and B or C and D respectively.

Turning now to FIG. 18, the linear voice settings 87 (i.e. the motive voice parameters) and the display features 83*a* to 83*f* will be described:

MAXIMUM NUMBER OF BIG OR SMALL INTERVALS IN A ROW [small (default=5), big (default=2)]

Those two numbers determine the interval-sizes in the linear-voices melody. With every small interval that is played, the likelihood for the following interval to be a small one decreases, the likelihood for the next interval being a big one increases. Every interval up to an extended four is regarded to be a small interval, while everything above is regarded to be a big interval.

MAX NO OF INTERVALS IN ONE DIRECTION: operates similar to the big and small interval-settings. With every interval up, the probability for a downward interval occurring increases. With every interval down, the probability for an interval going up increases. The speed of increase or decrease of probability to go into another direction is set by the maximum number of intervals in one direction.

FIRST PITCH: sets the first pitch of the voice.

CENTER-PITCH: sets the center pitch of the voice. This is the melodic center of the voice.

MIN PITCH: every note below this threshold will be transposed by an octave upwards MAX PITCH: every note above this threshold will be transposed by an octave downwards.

INTERVAL-PROBABILITY: sets the probability for each interval to be chosen relative to others.

These values influence the tonal output by means of weighted probability; understandably some of the values impose constraints into this process, whereas others have a weighted influence in the decision making process. The overall mechanism results in a tonal output, which has some controlled characteristics but is always evolving in a varying way.

Turning now to FIG. 8, the mapping device 48 will be described. The mapping device firstly receives the signals from the first output 30*a* of the integrator 20 representing averaged amplitude signals in four different frequency bands A, B, C and D. Such signals are supplied to a multiplier 82 which applies four user set multiplication factors 41 to the corresponding energy levels or amplitudes of these signals to generate four regulated band signals as an output. Such multiplication factors can also be pre-set by experts after performing an analysis of different noise environments. These four regulated band signals are applied respectively to an activating device 84 and a pattern recognition device 86.

Figure 9:
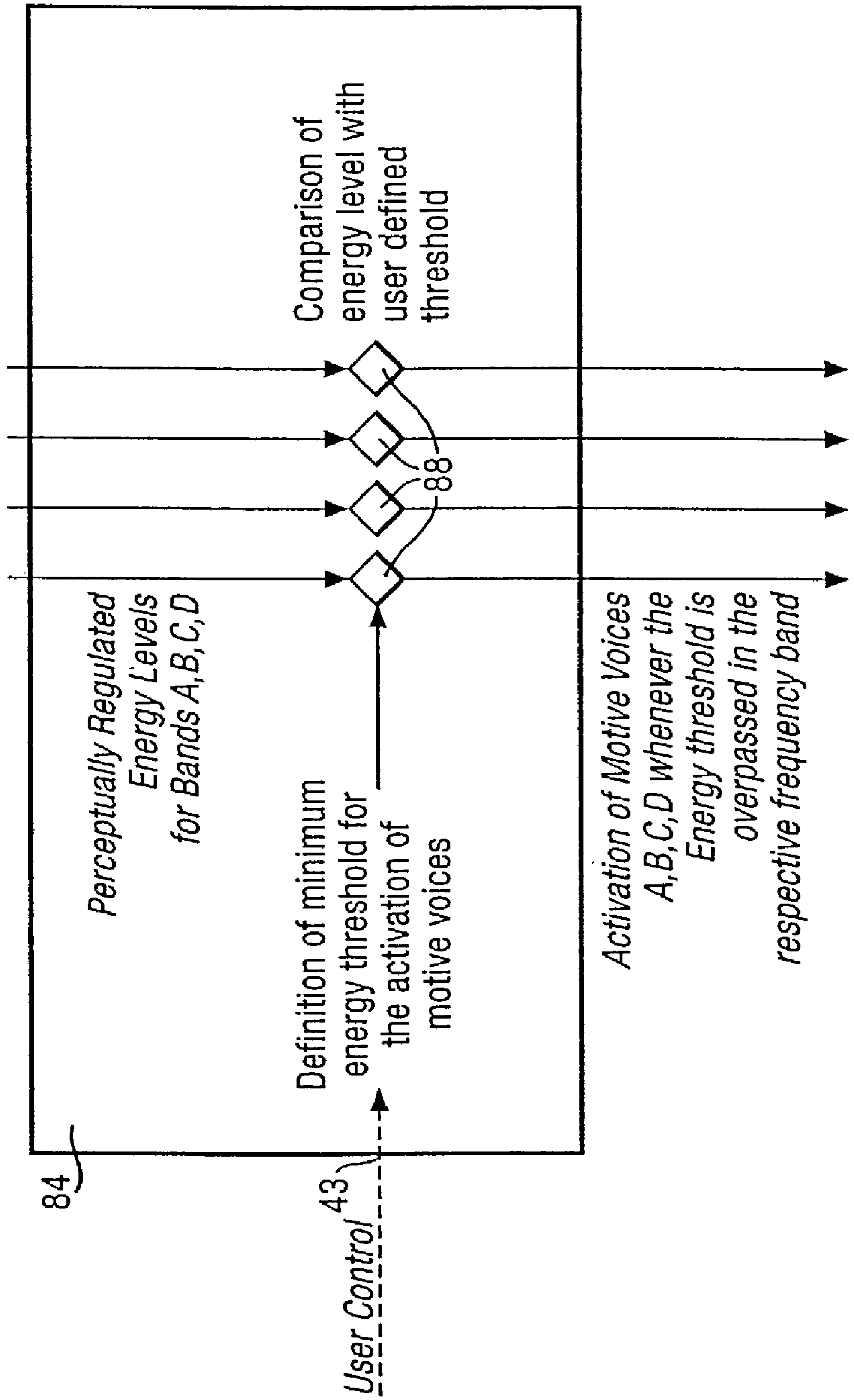
FIGS. 9 and 10 are block diagrams of sound activation and sound control arrangements, respectively, of the mapping device of FIG. 8.

The activating device 84 is further illustrated in FIG. 9 and includes a series of comparators 88 each set to compare the amplitudes of the regulated band signals with a single threshold level 43 set by the user. As soon as the threshold level 43 is exceeded in each case the respective comparator 88 issues a trigger signal for activating an associated one of the voice generators 60, 62, 64 or 66. Four motive voices may thereby be generated: motive voice A associated with band A, and motive voices B, C, D associated with bands B, C, D respectively.

Figure 10:
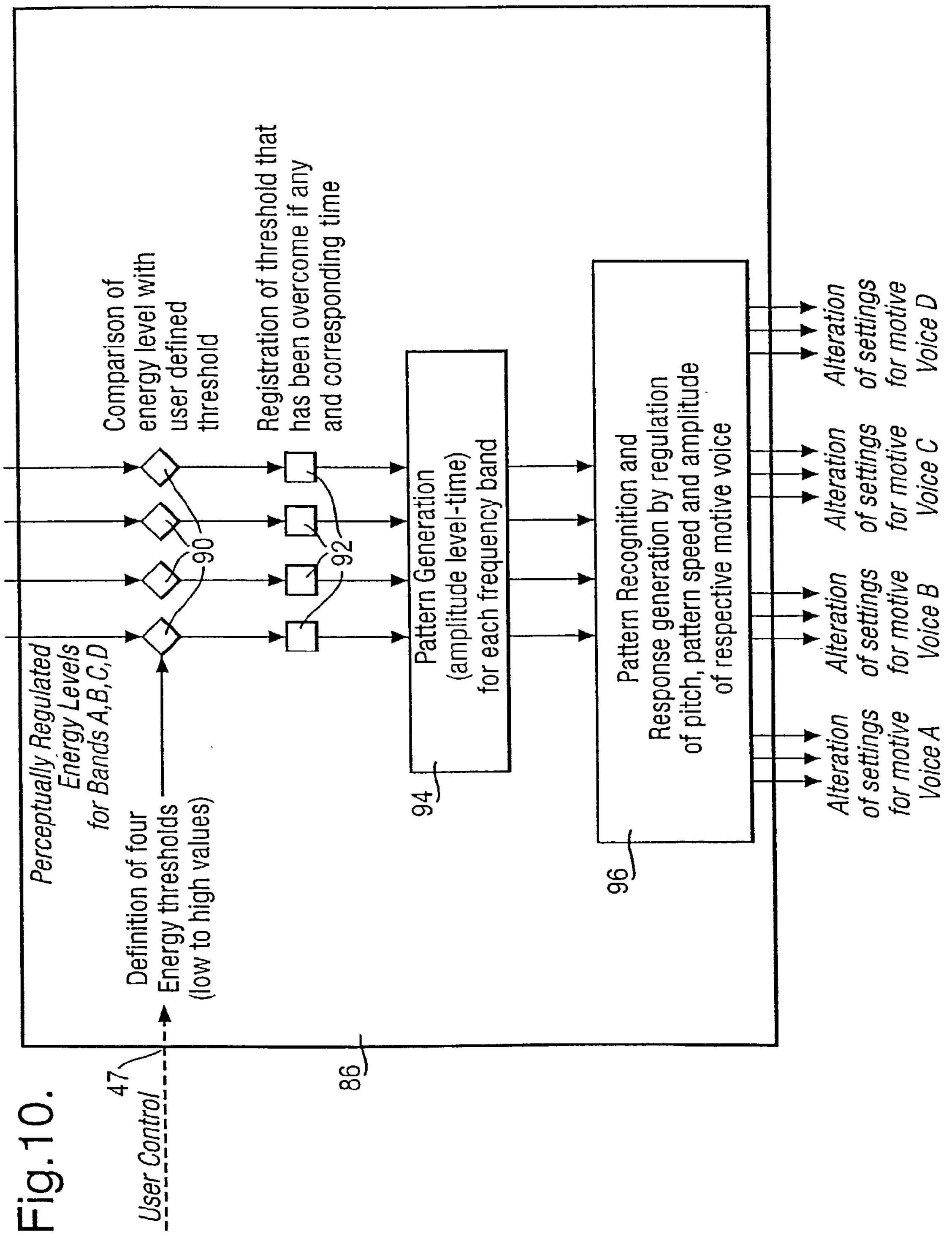

The pattern recognition arrangement 86 is further illustrated in FIG. 10 and comprises a series of comparators 90, each of which defines four user set threshold levels 47. The band regulation signals are supplied respectively to the comparators 90 where each band regulation signal is compared with each of the four threshold levels. A series of four timers 92 monitors the timing for each occasion that a threshold level is exceeded and a store 94 registers on each occasion and for each regulated band signal the threshold level that has been exceeded and the associated timing. A pattern recognition device 96 monitors the information contained in the store 94 and processes such information to provide four sets of outputs for regulating respectively the voice generators 60, 62 64 and 66.

The pattern recognition arrangement 86 operates on the basis of simple pattern recognition techniques to distinguish between noise environments by comparing energy level versus time patterns in certain frequency bands and to generate an appropriate response.

Reverting to FIG. 8, the mapping device 48 also receives the weighted Fourier transform signals from the output 30*c* of the interpreter 20 and applies these to an amplitude averaging arrangement 98 for performing averaging over a period of time frames 49 set by the user. The amplitude averaging arrangement 98 generates amplitude averaged signals as an output for the mapping device 48 for supply to the tonal sequence generator 50 for amplitude regulation of the signals from the voice generators 56 and 58. In addition, the mapping device 48 supplies an output based on the mapping of the pattern recognition arrangement 96 as feedback to the integration arrangement 30 for determining the four different frequency bands set in the integration arrangement 30.

Figure 15:
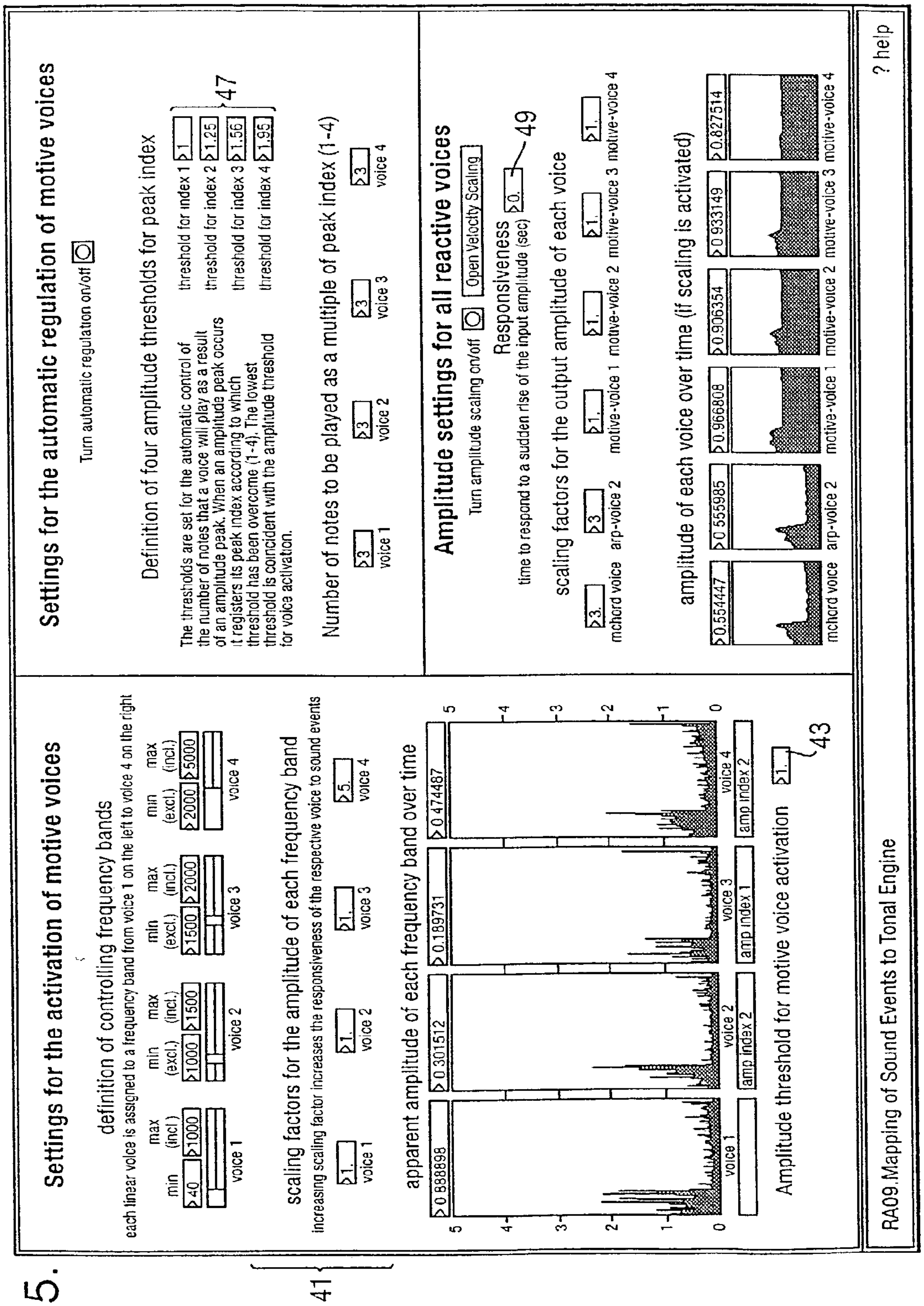
FIG. 15 is a view of a user adjustable display for inputting control functions to the mapping device of FIG. 8.

FIG. 15 shows, by way of example, a display available on the screen of the DSP 14, on which the possible inputs 41 to 47 are indicated and may be selected and variably set, for example by way of a mouse.

The voice generators 52 to 66 thus regulated as described above generate signals representing a tonal output for supply to the mixer 26. Likewise, the tonal sequence generator 50 generates via the setting circuit 70 a chord root signal for supply to the chord selection mechanism of the masking arrangement 22 in order to determine the 12 possible frequencies constituting list B described above.

The output of the DSP 14 constitutes the sound signals output from the mixer 26 for supply to the loudspeakers 16. It will be appreciated that these sound signals represent complex tonal sequences which are based on the input noise and on user input but which are pleasing to the ear.

In a preferred embodiment, more that one speaker device is provided for each of the tonal output and for the masker output. For example, four loudspeakers may be employed for the tonal output with different components of the tonal output being channeled to each one. This arrangement helps create a richer sound environment.

Figure 19:
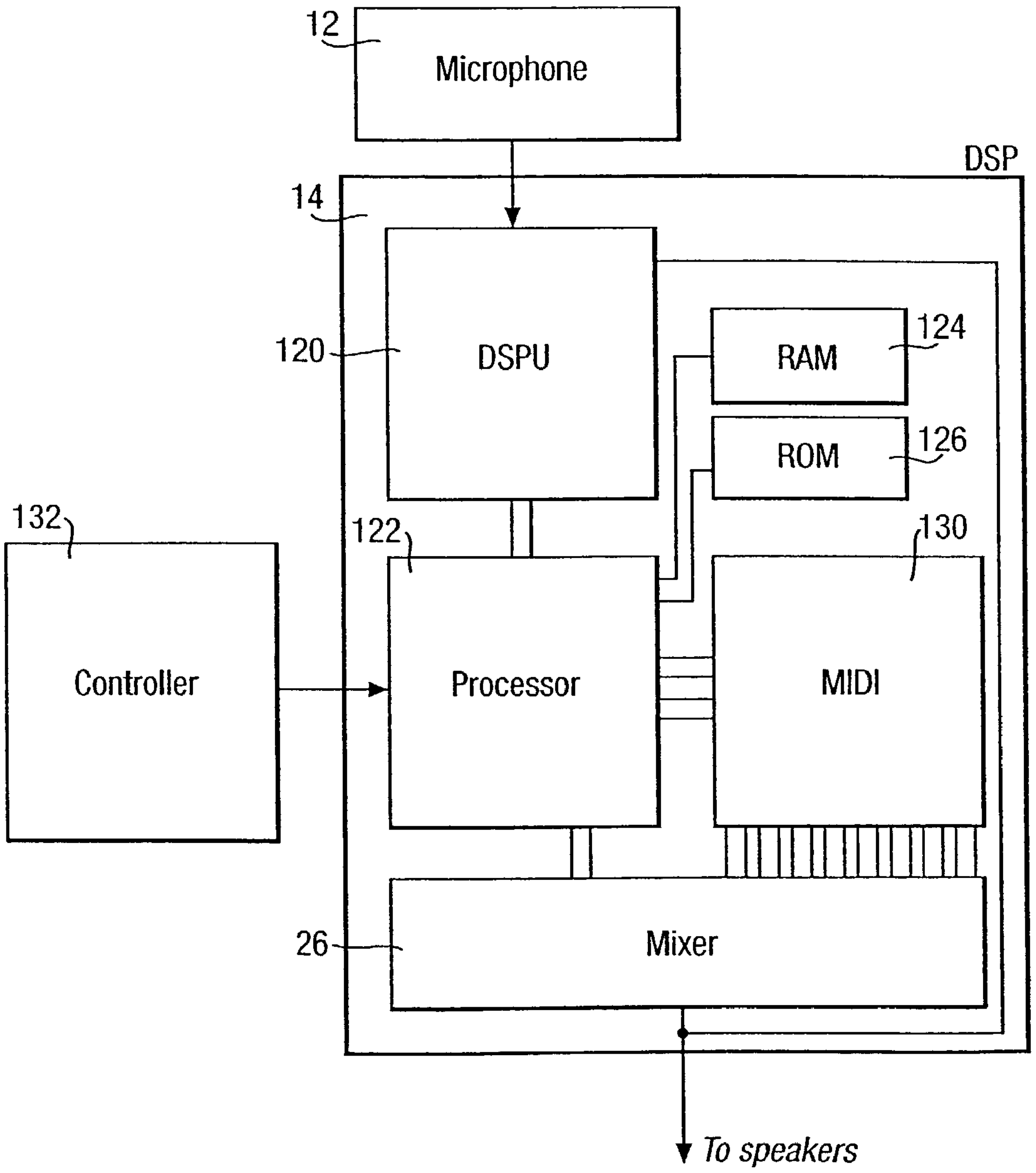
FIGS. 19 and 20 are block diagrams showing a practical embodiment of the signal processor of FIG. 3.

Turning now to FIGS. 19 to. 22, these show a practical embodiment of the digital signal processor described above with reference to FIGS. 3 to 18. Like parts are designated by the same reference numerals, and only the differences will be described.

Figure 20:
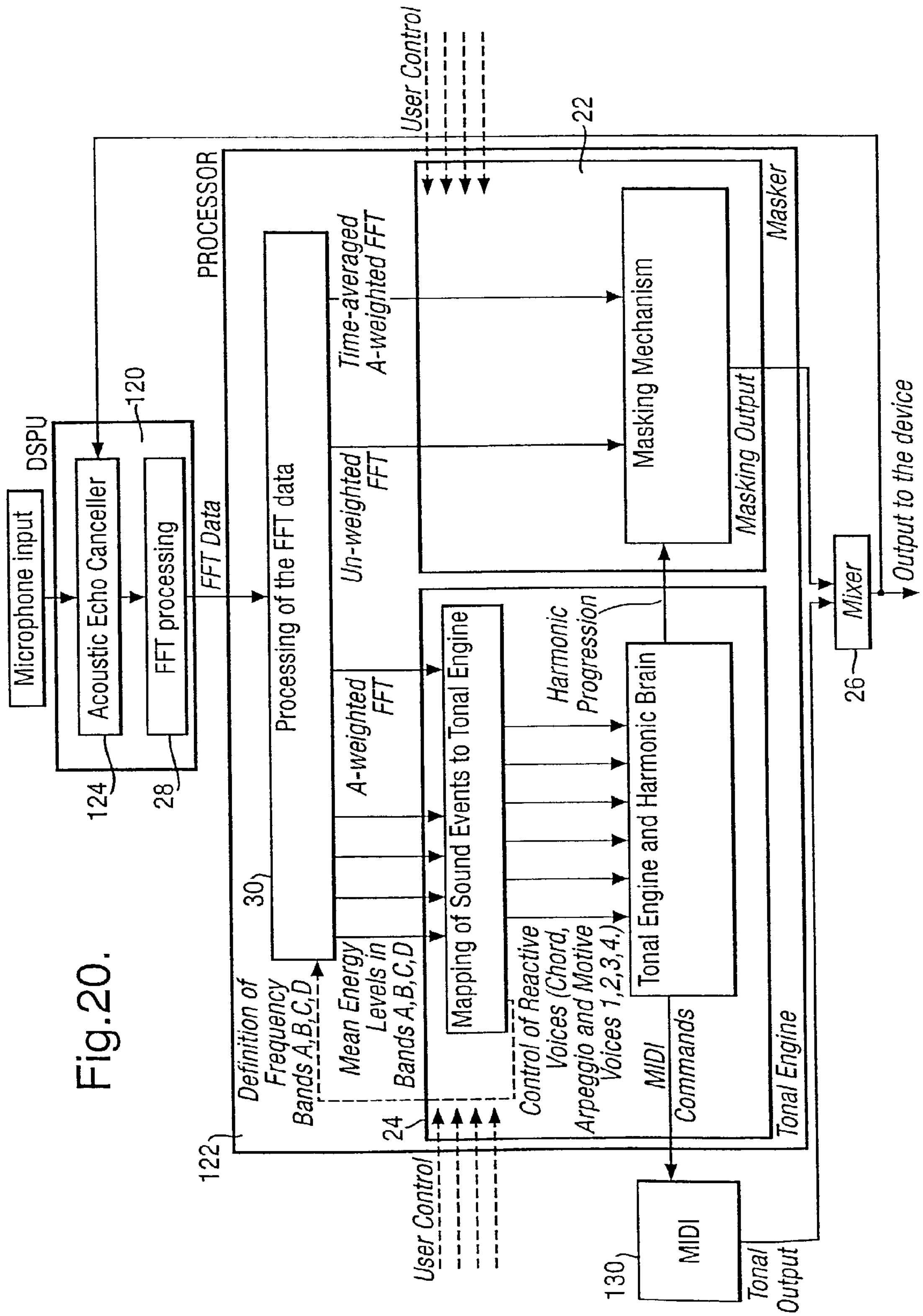

As illustrated in the FIGS. 19 and 20, the DSP 14 here comprises a digital signal processing unit 120 corresponding in part with the interpreter 20 and a processor 122 comprising the following circuits, namely, the integration arrangement 30, the masking arrangement 22 and the tonal engine 24. The processing unit 120 is designed to generate an accurate spectral representation of the sound environment picked up by the microphones 12, and comprises an acoustic echo canceller 124 as well as the fast Fourier transform processor 28 together with an internal or external ROM or EPROM. The processor 122 comprises a microprocessor unit for performing the arithmetic operations defined by the main subroutines of the algorithm as described above. For this purpose, the processor 122 employs a RAM 124 and a ROM 126, which may be either internal or external but which here are shown as external. The DSP 14 also includes a musical instrument digital interface unit (MIDI) 130, and the mixer 26 described above. A controller 132 is connected to the DSP 14 for providing the user inputs, for example, as described above with reference to FIGS. 14 to 18.

Figure 21:
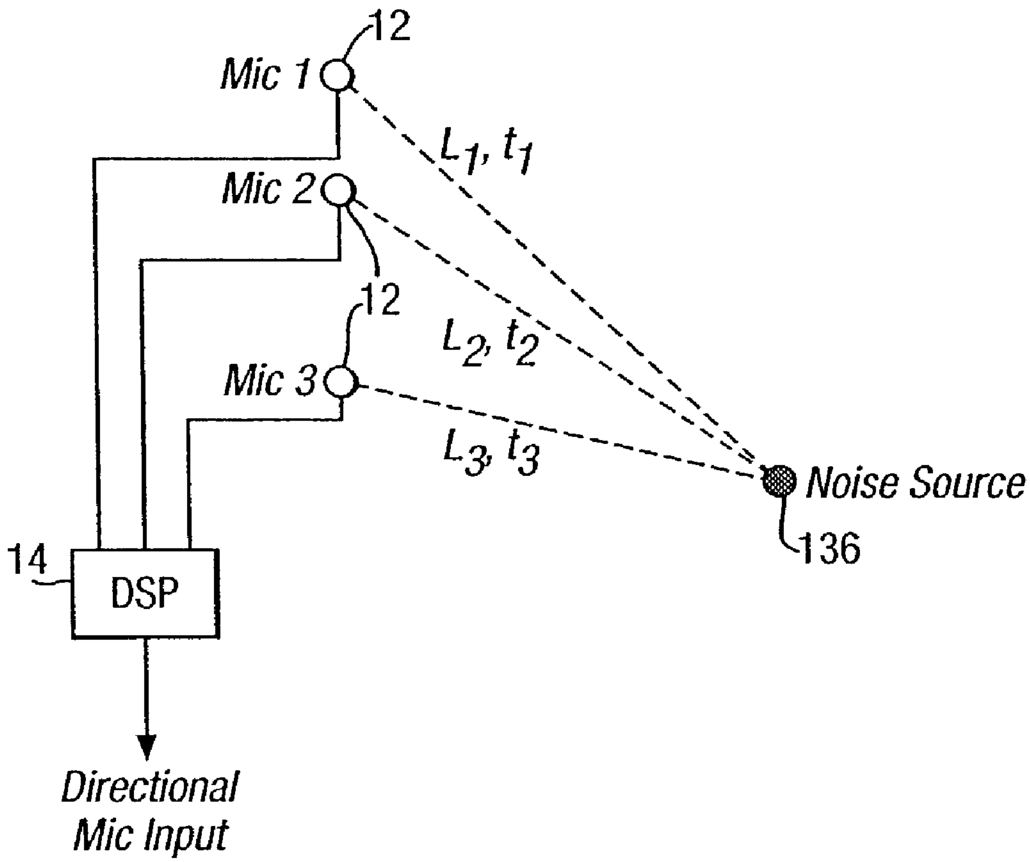
FIG. 21 is a diagram representing a preferred microphone arrangement for use with the processor of FIGS. 19 and 20.
Figure 21:
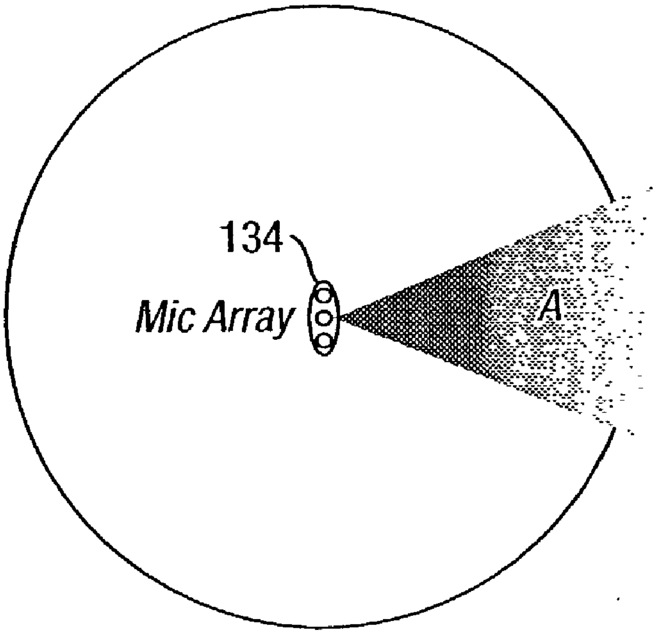

Turning to FIG. 21, the microphones 12 may be arranged in an array 134 so that they each have a different directional relationship with a noise source 136 in the sound environment. This enables the system to evaluate where the input noise is coming from for effecting a more accurate spectral analysis of the input noise signals, so that the system may respond selectively to noise generated in a particular location.

Figure 22:
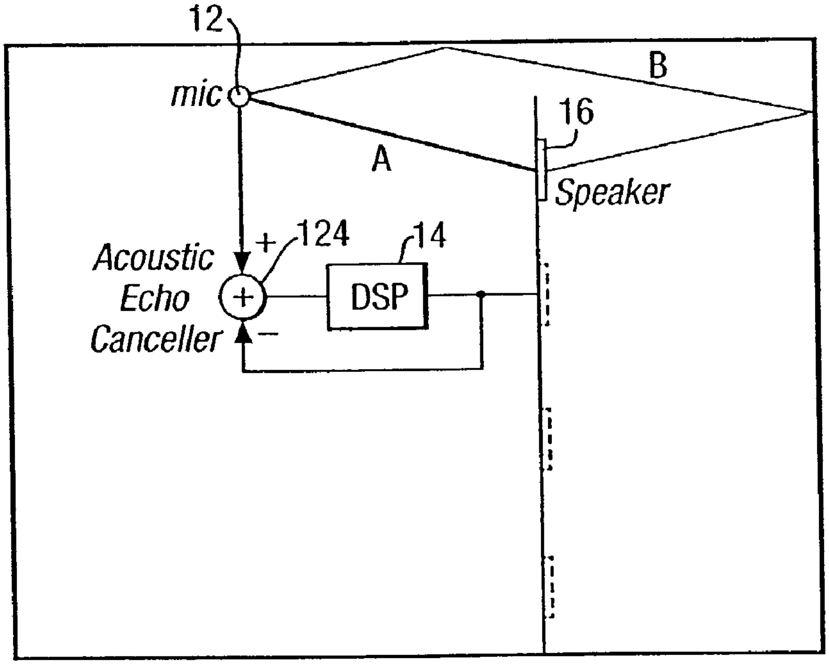
FIG. 22 is a diagram of an acoustic echo canceller of the processor of FIGS. 19 and 20.
Figure 23:
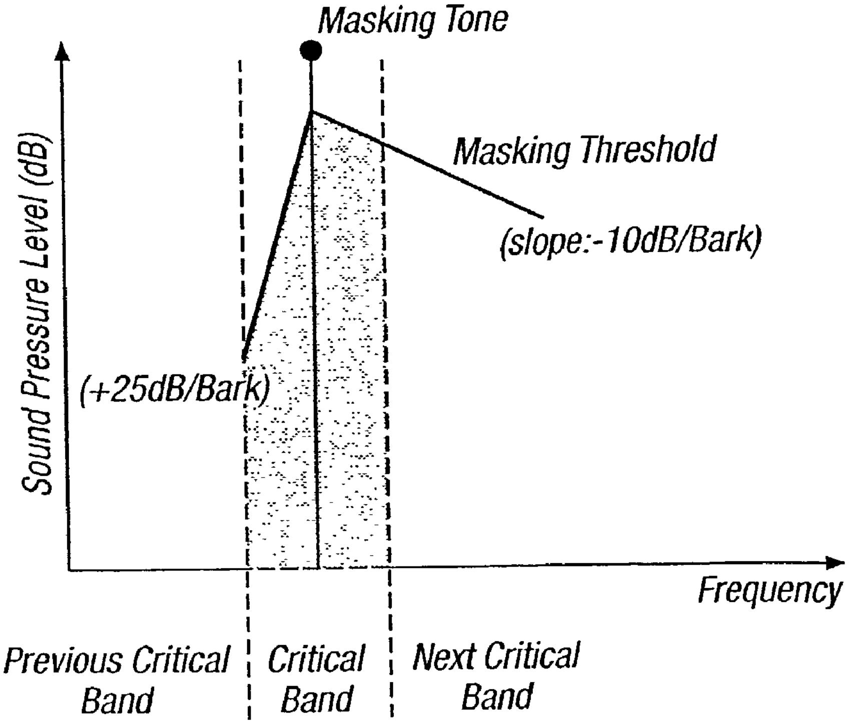
FIG. 23 is a graph showing a masking function.

Turning to FIG. 22, the function of the acoustic echo canceller 124 of the processing unit 120 will be described. As shown, the DSP 14 provides an output for supply to the loudspeakers 16 based on input signals received from the or each microphone 12. Sound generated by the loudspeakers 16 may be reflected back, for example along the line A and/or B, to the microphones 12. In order to cancel such an acoustic echo, the acoustic echo canceller 124 is provided in a feedback loop from the DSP 14 and the output signals from the DSP 14 are fed back to the acoustic echo canceller 124 for canceling the effects of acoustic echoes from the loudspeakers 16.

The MIDI 130 serves to synthesize signals output by the tonal engine 24 prior to these signals being supplied to the mixer 26. The MIDI 130 includes a RAM and a ROM containing a library of sound samples and a synthesis engine for generating the sound signals for supply to the loudspeakers 16. More especially the MIDI 130 is arranged to receive the output from the tonal output to the mixer 26, while the masking arrangement 22 is connected directly to the mixer 26.

All of the microphone array 134, the acoustic echo canceller 124 and the MIDI 130 are products which are commercially available.

Referring now to the controller 132 shown in FIG. 19, this may be employed to input the user settings described above with reference to the first embodiment of the invention as shown in FIGS. 3 to 15. However, the controller 132 may also be employed for the input of other sets of parameters that define the behavior of the electronic sound system according to the invention. These sets of parameters are termed "presets", and such presets may be downloaded into the controller 132 or into the DSP 14 from the internet or web or by way of modem connections or using peripherals such as memory cards or other software carrying devices.

The embodiment of the invention shown in FIGS. 19 to 22 therefore operates substantially as has been generally described with reference to FIGS. 3 to 18.

It will be appreciated that the DSP described above has been described largely in terms of the hardware required to implement the invention. It will, of course, be appreciated that the invention could also be implemented by appropriate software for performing the functions in the sequence described above.

The present invention readily lends itself to a modular construction and this has a number of advantages in terms of upgradability and interchangeability. A matrix of hardware and software components can be generated, the combination of which can result in different products with different capabilities.

Various modifications are also possible:

For example, the microphones may be omitted, or they may be included but the DSP 14 may have no capability for tonal sequence generation. In the first case, the system would generate masker sounds and tonal sequences without responding to sensed noise, responding instead only to the user settings or to pre-programmed presets, to create a rich and stimulating sound environment. In the second case, the system might have a downgraded DSP 14, which would lack the MIDI chipset and would probably feature a less powerful processor and less RAM/ROM.

Similarly, there might be scope for different versions of the algorithm to be available, either lacking the tonal engine altogether, or having a stripped down version of it that would rely on a less sophisticated mapping mechanism. This can also be achieved by having a modular design for the algorithm software, designed to ensure that all the algorithm subroutines refer to a main structure that allows for various software modules to be used independently.

Another possibility is for the system to operate in an interactive mode with the surrounding noise/sound environment. Various options are possible through modification either of the masker output, by employing a different function for the chord selection mechanism 38 and the amplitude averaging mechanism 42, or the tonal engine output by employing different settings in the mapping sub-routine and a different arrangement for supplying the control data from the mapping device 48 to the tonal engine 50. particularly to the four motive voices generators 60 to 68.

One possibility for such an interactive model based on the tonal output features the activation of four linear voices, each one assigned to a respective frequency band. The relationship between the voices and the frequency bands is twofold: each voice is triggered if the mean energy in the frequency band trespasses a set threshold; and its tonal output is in the same frequency range as the activity in the frequency band. This model can afford dynamic regulation of the amplitude of the output according to the sensed input. When increased activity is sensed by the mechanism 86 for responding to prominent auditory cues, certain characteristics of the motive voices (pattern, pattern speed) are changed in order better to interact with the sensed noise. Ultimately all the parameters of the reactive voices may be automatically adjusted.

In this instance, the wider the spectrum that constitutes distraction, the more output streams you have to interact with it. A main aim of this arrangement is to achieve spectral integration by offering neighboring frequency components that the disturbing sounds can group with. Also it may increase the possibility of achieving "masking by chance"; if there is a tonal output in the frequency range of speech activity, then outputting tones in the same range may partially mask speech.

Another possibility for such an interactive model employs four linear voices, all of them being assigned to the same frequency band. For example, this model may focus on the 200 and 4000 Hz range where most speech occurs. In this example, there are four thresholds that trigger the four respective voices. The linear voices are arranged to be sequentially triggered one after the other, when each threshold is overcome.

Two of the voices can then be used for spectral integration and two, clearly segregated from the sensed signal, for attracting attention.

In this instance, the more the energy in the sensed noise environment, the more output streams the tonal engine produces to provide alternative streams for the listener to engage with. The main aim here is to increase the possibility of achieving "Masking by chance"; if there is tonal output in the frequency range of speech activity, then outputting tones in the same range may partially mask speech. Another aim is to rely on the triggering of schemas and make sure that there are always enough cues in the sound environment for the listener to follow when noise levels/activity are increased.

Although the invention has been particularly shown and described with reference to several preferred embodiments thereof, it will be understood by those skilled in the art that various changes in form and details may be made therein without departing from the spirit and scope of the invention as defined in the appended claims.

We claim:

1. An electronic sound screening system for regulating sound in an environmental space, comprising:

means for receiving acoustic energy representing ambient sound from the environmental space and converting such energy into input electrical signals, means for performing an analysis of said input electrical signals in order to detect frequency and amplitude characteristics of the acoustic energy and for generating corresponding data analysis signals, means for receiving the data analysis signals and for monitoring predetermined frequency and amplitude characteristics of the electrical signals on the basis of the data analysis signals and for generating a real-time sound control output, sound creating means responsive to the sound control output for generating signals representing sound and for regulating the sound signals according to the sound control output, the sound creating means comprising at least one of a masking arrangement for generating masking signals representing masking sounds that have a selected relationship with the predetermined characteristics and a tonal engine for generating tonal sequence signals representing tonal sequences, and output means for converting the sound signals into sound and supplying such sound to the environmental space, whereby to regulate ambient sound characteristics in the environmental space in real-time.

2. A sound screening system according to claim 1, wherein the means for performing an analysis are arranged to perform Fourier transform processing.

3. A sound screening system according to claim 1, wherein the masking arrangement is arranged to detect disturbances in the input acoustic energy.

4. A sound screening system according to claim 1, wherein the masking arrangement is arranged to regulate the spectral content and/or the amplitude level of the output sound signals.

5. A sound screening system according to claim 1, wherein the monitoring means comprises a selection arrangement for locating respective cues in the input signals and wherein the sound creating means are arranged to impose a sound structure on the sound signals on the basis of the respective cues.

6. A sound screening system according to claim 5, wherein the respective cues in the input signals comprise prominent frequencies.

7. A sound screening system according to claim 5, wherein the respective cues comprise sound events.

8. A sound screening system according to claim 5, wherein the sound creating means is arranged to impose a tonal structure on the sound signals on the basis of the respective cues.

9. A sound screening system according to claim 8, wherein the tonal structure comprises pace and rhythm sequences.

10. A sound screening system according to claim 8, wherein the tonal structure comprises sequences representing spectral and/or temporal groupings of auditory responses.

11. A sound screening system according to claim 8, wherein the tonal structure comprises sequences representing at least one of a harmonic progression of notes, a chord voice, and an arpeggio voice.

12. A sound screening system according to claim 8, wherein the tonal structure is determined on the basis of probability weightings.

13. A sound screening system according to claim 12, wherein the tonal structure is determined from selected probability tables.

14. A sound screening system according to claim 1, wherein the tonal engine comprises a mapping device responsive to the data analysis signals for performing pattern recognition and for generating corresponding control signals for controlling the tonal sequence signals.

15. A sound screening system according to claim 1, wherein the means for receiving acoustic energy comprise a microphone system having at least one microphone arranged to generate plural input electrical signals representing a directional input of acoustic energy.

16. A sound screening system according to claim 1, further comprising a controller for providing a control input.

17. A sound screening system according to claim 16, wherein the controller is responsive to a manually settable user input.

18. A sound screening system according to claim 16, wherein the controller is responsive to instructions received by means of at least one of: an internet connection, a modem, a radio connection, a cable connection and a memory device for providing the control input.

19. A sound screening system according to claim 16, further comprising a memory store for recording the control input.

20. A sound screening system according to claim 1, further comprising a pre-programmed memory device for providing a control input.

21. A sound screening system according to claim 1, further comprising:

means for receiving a control input representing selected sound parameters, and means responsive to the control input for providing corresponding control signals, the tonal engine comprising a plurality of sound generators responsive to the control signals for generating tonal sequence signals representing tonal sequences based on the selected sound parameters.

22. A sound screening system according to claim 21, wherein the control input also represents probability functions, and in which the sound generators are arranged to generate the tonal sequence signals on the basis of probability weightings.

23. A sound screening system according to claim 21, further comprising means for providing the control input comprising manually adjustable input means for permitting user setting of the sound screening system.

24. A sound screening system according to claim 23, wherein the means for providing the control input comprises a memory device.

25. A method of regulating sound in an environmental space comprising the steps of:

receiving acoustic energy representing ambient sound from the environmental space;

converting said received acoustic energy into input electrical signals;

analyzing said input electrical signals in order to detect frequency and amplitude characteristics of the acoustic energy;

generating data analysis signals based on said analyzing;

monitoring predetermined frequency and amplitude characteristics of the electrical signals on the basis of the data analysis signals;

generating a real-time sound control output;

generating at least one of masking signals representing masking sounds that have a selected relationship with the predetermined characteristics and tonal sequence signals representing tonal sequences; and producing, in response to the sound control output, sound signals representing sound, the sound signals being regulated according to the sound control output.

26. The method of claim 25, further comprising the step of outputting said sound signals as sound.

27. The method of claim 25, wherein the step of analyzing comprises the step of performing a Fourier transformation.

28. The method of claim 25, wherein the step of analyzing comprises the step of detecting disturbances in the electrical signal.

29. The method of claim 25, further comprising the step of regulating a spectral content and/or an amplitude level of said sound signals.

30. The method of claim 25, wherein the step of producing comprises the steps of:

locating respective cues; and imposing a sound structure on said sound signals on the basis of the respective cues.

31. The method of claim 30, wherein the respective cues comprise prominent frequencies.

32. The method of claim 30, wherein the respective cues comprise sound events.

33. The method of claim 30, wherein said sound structure comprises a tonal structure.

34. The method of claim 33, wherein the step of producing comprises the step of generating tonal sequence signals.

35. The method of claim 34, wherein the step of producing further comprises the steps of:

performing pattern recognition; and generating corresponding control signals for controlling the tonal sequence signals.

36. The method of claim 33, wherein the tonal structure comprises pace and rhythm sequences.

37. The method of claim 33, wherein the tonal structure comprises sequences representing spectral and/or temporal groupings of auditory responses.

38. The method of claim 33, wherein the tonal structure comprises sequences representing at least one of a harmonic progression of notes, a chord voice, and an arpeggio voice.

39. The method of claim 33, wherein the tonal structure is determined on the basis of probability weightings.

40. The method of claim 33, wherein the tonal structure is determined from selected probability tables.

* * * * *